(12) United States Patent
Harshman et al.

(10) Patent No.: US 12,114,916 B2
(45) Date of Patent: Oct. 15, 2024

(54) CATHETER AND HANDLE ASSEMBLY, SYSTEMS, AND METHODS

(71) Applicant: Holaira, Inc., Plymouth, MN (US)

(72) Inventors: Scott Harshman, Kirkland, WA (US); Richard C. Gunderson, Maple Grove, MN (US); John Streeter, Plymouth, MN (US); Martin L. Mayse, Wayzata, MN (US); Mark R Bilitz, Plymouth, MN (US); Matt Heidner, Maple Grove, MN (US); Steven P. Mertens, Plymouth, MN (US); Larry Wales, Plymouth, MN (US)

(73) Assignee: Nuvaira, Inc., Plymouth, MN (US)

( * ) Notice: Subject to any disclaimer, the term of this patent is extended or adjusted under 35 U.S.C. 154(b) by 79 days.

(21) Appl. No.: 15/103,500

(22) PCT Filed: Dec. 12, 2014

(86) PCT No.: PCT/US2014/069971
§ 371 (c)(1),
(2) Date: Jun. 10, 2016

(87) PCT Pub. No.: WO2015/089377
PCT Pub. Date: Jun. 18, 2015

(65) Prior Publication Data
US 2016/0310210 A1    Oct. 27, 2016

Related U.S. Application Data

(60) Provisional application No. 61/915,282, filed on Dec. 12, 2013.

(51) Int. Cl.
*A61B 18/14*    (2006.01)
*A61B 1/00*    (2006.01)
(Continued)

(52) U.S. Cl.
CPC ...... *A61B 18/1492* (2013.01); *A61B 1/00032* (2013.01); *A61B 1/0011* (2013.01);
(Continued)

(58) Field of Classification Search
CPC ... A61B 1/018; A61B 1/2676; A61B 1/00114; A61B 1/00128; A61B 1/00124;
(Continued)

(56) References Cited

U.S. PATENT DOCUMENTS 5,066,295 A * 11/1991 Kozak .................... A61B 18/14
                                                        606/47
5,599,300 A *  2/1997 Weaver ............. A61B 18/1492
                                                       128/898
(Continued)

FOREIGN PATENT DOCUMENTS

EP    1 864 621 A1    12/2007
EP    1870051 A1      12/2007
(Continued)

OTHER PUBLICATIONS

Office Action dated Mar. 9, 2018 for Chinese Application No. 201480068344.4, 8 pages.
(Continued)

*Primary Examiner* — Jaymi E Della
(74) *Attorney, Agent, or Firm* — Husch Blackwell LLP

(57) ABSTRACT

A catheter and handle assembly for use in treating tissue. More specifically, the invention relates to a catheter assembly having an elongate shaft, ablation assembly coupled to one end of the shaft, and a handle coupled to the other end of the shaft. The handle facilitates both axial and circumferential positioning of the ablation assembly via the shaft in an airway, conduit, or vessel for treatment of the tissue. Embodiments include the use of a handle to facilitate the axial and circumferential positioning of the shaft and abla-
(Continued)

tion assembly through and independent of a working channel of a bronchoscope during treatment for pulmonary disease like COPD and asthma.

24 Claims, 18 Drawing Sheets

(51) Int. Cl.
*A61B 1/018* (2006.01)
*A61B 1/267* (2006.01)
*A61B 18/00* (2006.01)
*A61B 18/18* (2006.01)
*A61B 90/00* (2016.01)

(52) U.S. Cl.
CPC ...... *A61B 1/00114* (2013.01); *A61B 1/00128* (2013.01); *A61B 1/00133* (2013.01); *A61B 1/018* (2013.01); *A61B 1/2676* (2013.01); *A61B 2018/00023* (2013.01); *A61B 2018/00214* (2013.01); *A61B 2018/00434* (2013.01); *A61B 2018/00541* (2013.01); *A61B 2018/00577* (2013.01); *A61B 2018/0091* (2013.01); *A61B 2018/00982* (2013.01); *A61B 18/1815* (2013.01); *A61B 2090/064* (2016.02); *A61B 2090/3966* (2016.02)

(58) Field of Classification Search
CPC .... A61B 2018/0091; A61B 2018/1861; A61B 2018/00982; A61B 2018/00172; A61B 2018/00178; A61B 2018/00184; A61B 2018/0096; A61B 2018/00202; A61B 2018/00214; A61B 2018/0022; A61B 2018/0094; A61B 2018/00946; A61B 2018/00952
See application file for complete search history.

(56) References Cited

U.S. PATENT DOCUMENTS

| | | | |
|---|---|---|---|
| 5,843,091 A * | 12/1998 | Holsinger | A61B 18/1492 606/108 |
| 6,023,989 A * | 2/2000 | Imase | F16H 55/10 74/422 |
| 6,352,539 B1 * | 3/2002 | Avellanet | A61F 2/86 606/113 |
| 7,198,625 B1 * | 4/2007 | Hui | A61B 18/1482 606/41 |
| 7,608,275 B2 | 10/2009 | Deem et al. | |
| 8,088,127 B2 | 1/2012 | Mayse et al. | |
| 8,133,497 B2 | 3/2012 | Deem et al. | |
| 8,172,827 B2 | 5/2012 | Deem et al. | |
| 8,226,638 B2 | 7/2012 | Mayse et al. | |
| 8,338,164 B2 | 12/2012 | Deem et al. | |
| 8,483,831 B1 | 7/2013 | Hlavka et al. | |
| 8,489,192 B1 | 7/2013 | Hlavka et al. | |
| 8,660,647 B2 | 2/2014 | Parnis et al. | |
| 8,731,672 B2 | 5/2014 | Hlavka et al. | |
| 8,740,895 B2 | 6/2014 | Mayse et al. | |
| 8,777,943 B2 | 7/2014 | Mayse et al. | |
| 8,808,280 B2 | 8/2014 | Mayse et al. | |
| 8,821,489 B2 | 9/2014 | Mayse et al. | |
| 8,911,439 B2 | 12/2014 | Mayse et al. | |
| 8,932,289 B2 | 1/2015 | Mayse et al. | |
| 8,961,391 B2 | 2/2015 | Deem et al. | |
| 8,961,507 B2 | 2/2015 | Mayse et al. | |
| 8,961,508 B2 | 2/2015 | Mayse et al. | |
| 9,005,195 B2 | 4/2015 | Mayse et al. | |
| 9,017,324 B2 | 4/2015 | Mayse et al. | |
| 9,125,643 B2 | 9/2015 | Hlavka et al. | |
| 9,149,328 B2 | 10/2015 | Dimmer et al. | |
| 9,339,618 B2 | 5/2016 | Deem et al. | |
| 9,398,933 B2 | 7/2016 | Mayse | |
| 9,498,283 B2 | 11/2016 | Deem et al. | |
| 9,539,048 B2 | 1/2017 | Hlavka et al. | |
| 9,649,153 B2 | 5/2017 | Mayse et al. | |
| 9,649,154 B2 | 5/2017 | Mayse et al. | |
| 9,662,171 B2 | 5/2017 | Dimmer et al. | |
| 9,668,809 B2 | 6/2017 | Mayse et al. | |
| 9,675,412 B2 | 6/2017 | Mayse et al. | |
| 9,867,986 B2 | 1/2018 | Hlavka et al. | |
| 9,931,162 B2 | 4/2018 | Mayse et al. | |
| 10,022,529 B2 | 7/2018 | Deem et al. | |
| 10,149,714 B2 | 12/2018 | Mayse et al. | |
| 10,201,386 B2 | 2/2019 | Mayse et al. | |
| 10,206,735 B2 | 2/2019 | Kaveckis et al. | |
| 2004/0054368 A1 * | 3/2004 | Truckai | A61B 18/082 606/41 |
| 2004/0106920 A1 * | 6/2004 | Jenkins | A61B 18/1492 606/49 |
| 2004/0226556 A1 | 11/2004 | Deem et al. | |
| 2006/0225742 A1 | 10/2006 | Deem et al. | |
| 2007/0255311 A1 * | 11/2007 | Hiraoka | A61B 1/00137 606/205 |
| 2007/0293857 A1 * | 12/2007 | Blind | A61B 18/1492 606/45 |
| 2008/0033238 A1 * | 2/2008 | Takahashi | A61B 17/072 600/106 |
| 2008/0242925 A1 * | 10/2008 | Suda | A61B 10/04 600/104 |
| 2008/0306334 A1 * | 12/2008 | Okada | A61B 18/1492 600/104 |
| 2010/0081987 A1 | 4/2010 | Christian | |
| 2010/0185161 A1 * | 7/2010 | Pellegrino | A61B 17/3472 604/272 |
| 2011/0077591 A1 | 3/2011 | Plicchi et al. | |
| 2011/0082453 A1 | 4/2011 | Fischer et al. | |
| 2011/0152855 A1 * | 6/2011 | Mayse | A61B 18/1492 606/33 |
| 2011/0178569 A1 | 7/2011 | Parnis et al. | |
| 2011/0257647 A1 | 10/2011 | Mayse et al. | |
| 2011/0301587 A1 | 12/2011 | Deem et al. | |
| 2011/0319709 A1 * | 12/2011 | Suzuki | A61B 18/1477 600/104 |
| 2012/0016364 A1 | 1/2012 | Mayse et al. | |
| 2012/0160364 A1 | 1/2012 | Mayse et al. | |
| 2012/0101485 A1 * | 4/2012 | Wittenberger | A61B 18/02 606/21 |
| 2012/0130458 A1 * | 5/2012 | Ryba | A61B 18/02 607/105 |
| 2012/0221087 A1 | 8/2012 | Parnis et al. | |
| 2012/0289901 A1 * | 11/2012 | Fink | A61B 10/0283 604/117 |
| 2012/0302909 A1 | 11/2012 | Mayse et al. | |
| 2012/0316552 A1 | 12/2012 | Mayse et al. | |
| 2013/0110104 A1 | 5/2013 | Corvi et al. | |
| 2013/0289556 A1 | 10/2013 | Mayse et al. | |
| 2013/0310822 A1 | 11/2013 | Mayse et al. | |
| 2014/0371809 A1 | 12/2014 | Parnis et al. | |
| 2016/0022351 A1 | 1/2016 | Kaveckis et al. | |
| 2016/0038725 A1 | 2/2016 | Mayse et al. | |
| 2016/0220851 A1 | 8/2016 | Mayse et al. | |
| 2016/0278845 A1 | 9/2016 | Mayse | |
| 2017/0014571 A1 | 1/2017 | Deem et al. | |
| 2017/0050008 A1 | 2/2017 | Mayse | |
| 2017/0245911 A1 | 8/2017 | Mayse et al. | |
| 2018/0028748 A1 | 2/2018 | Deem et al. | |
| 2018/0042668 A1 | 2/2018 | Dimmer et al. | |
| 2018/0133475 A1 | 5/2018 | Hlvaka et al. | |
| 2018/0199993 A1 | 7/2018 | Mayse et al. | |

FOREIGN PATENT DOCUMENTS

| | | |
|---|---|---|
| EP | 1892010 A1 | 2/2008 |
| EP | 2014218 A2 | 1/2009 |
| EP | 2 022 431 A1 | 11/2009 |
| JP | A 2006 187471 | 7/2006 |
| JP | A 2006 288755 | 10/2006 |
| JP | A 2008 049160 | 3/2008 |
| JP | A 2009 539552 | 11/2009 |

(56) References Cited

FOREIGN PATENT DOCUMENTS

| | | |
|---|---|---|
| JP | A 2013 508121 | 3/2013 |
| WO | WO0066017 | 11/2000 |
| WO | WO 2007/149263 A1 | 12/2007 |
| WO | WO 2011/056684 A2 | 5/2011 |

OTHER PUBLICATIONS

International Search Report (PCT/ISA/210) for International Application No. PCT/US2014/069971 mailed Mar. 24, 2015.
Written Opinion (PCT/ISA/237) for for International Application No. PCT/US2014/069971 mailed Mar. 24, 2015.
Search Report dated Jul. 21, 2017 for EP Application No. 14868867.5, 7 pages.
Office Action dated Sep. 25, 2018 for Japanese Application No. 2016-538675, 12 pages.
Office Action dated Dec. 3, 2018 for Chinese Application No. 201480068344.4, 9 pages.
Office Action dated Sep. 3, 2019 for Japanese Application No. 2016538675, 12 pages.
Office Action dated Dec. 10, 2019 for Chinese Application No. 201480068344.4, 5 pages.
Office Action dated May 8, 2019 for Chinese Application No. 20140068344.4, 19 pages.
International Preliminary Report on Patentability No. PCT/US2014/069971, mailed on Jun. 23, 2016, 8 pages.

\* cited by examiner

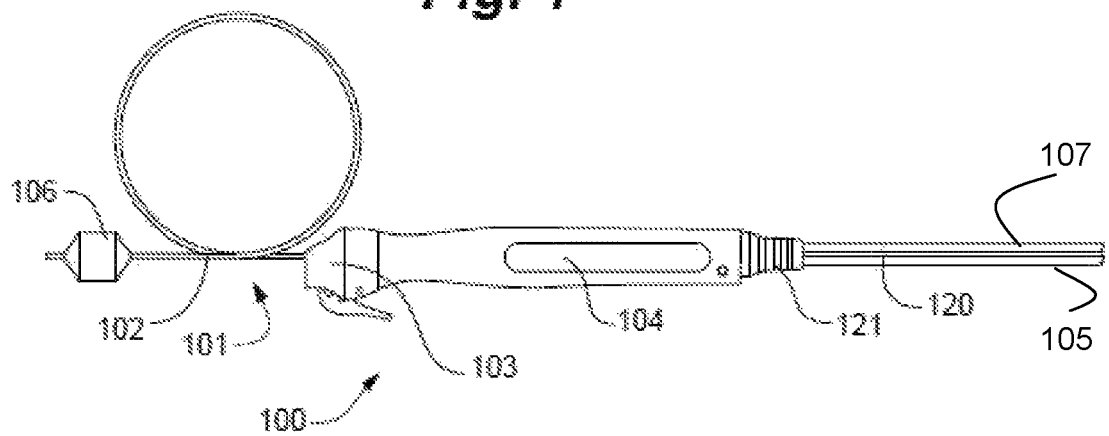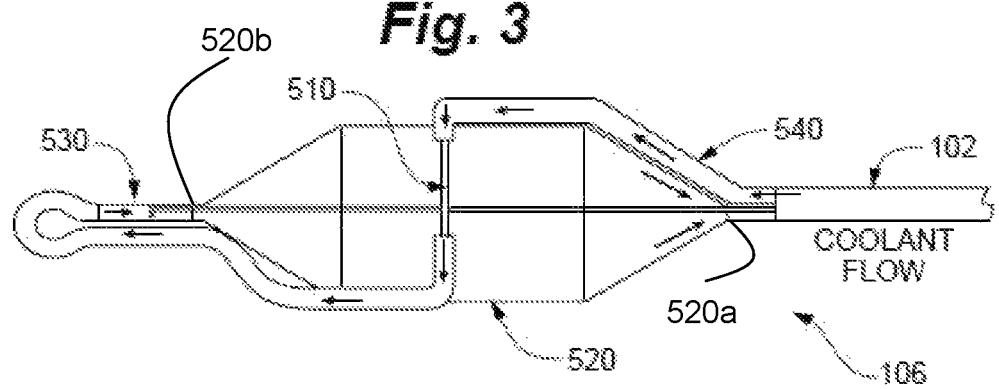

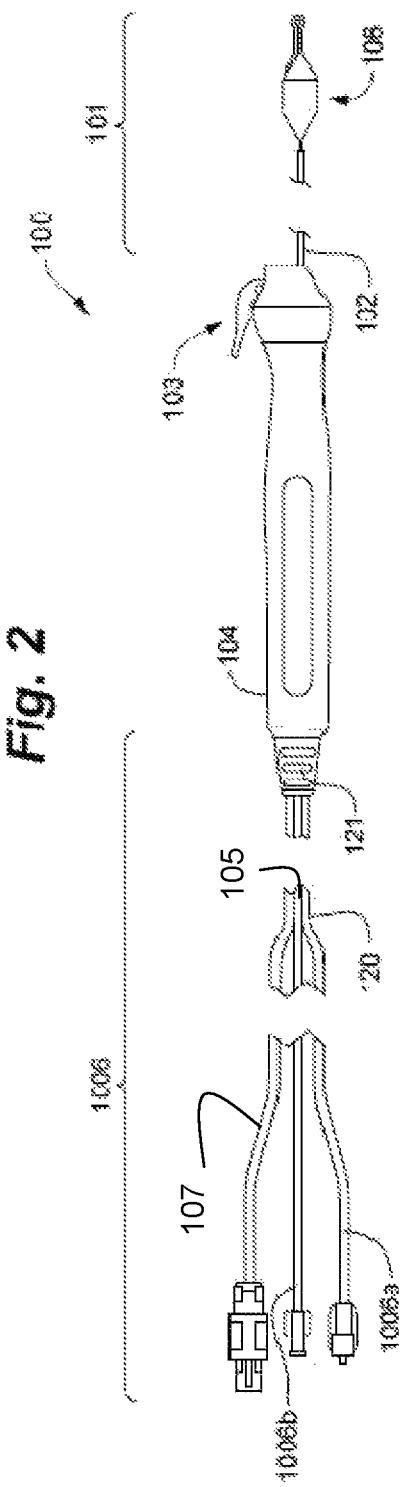

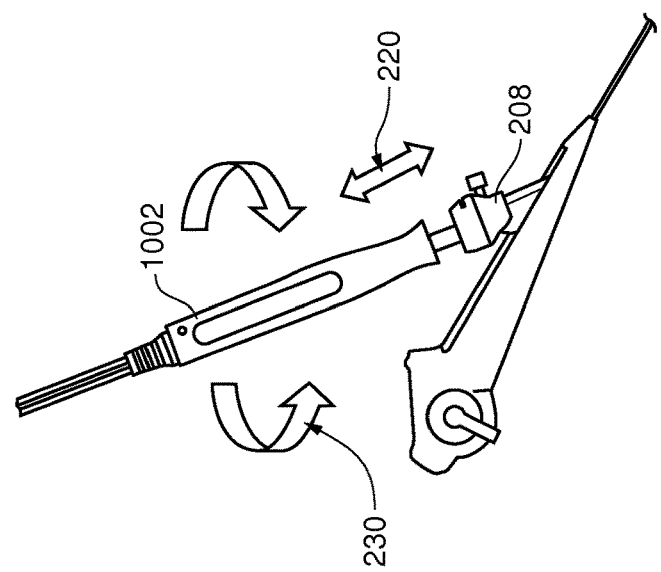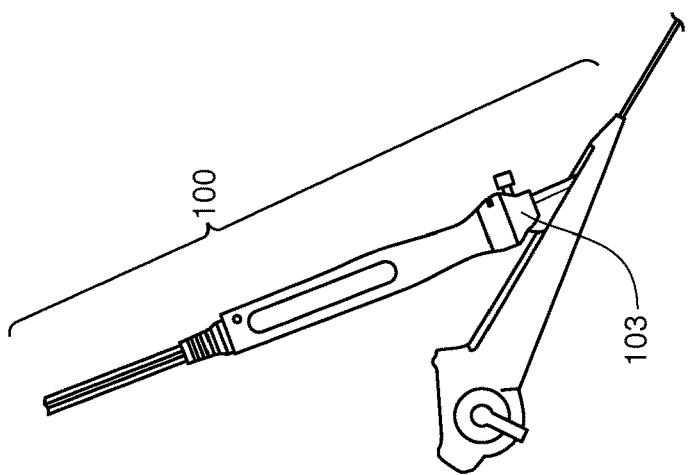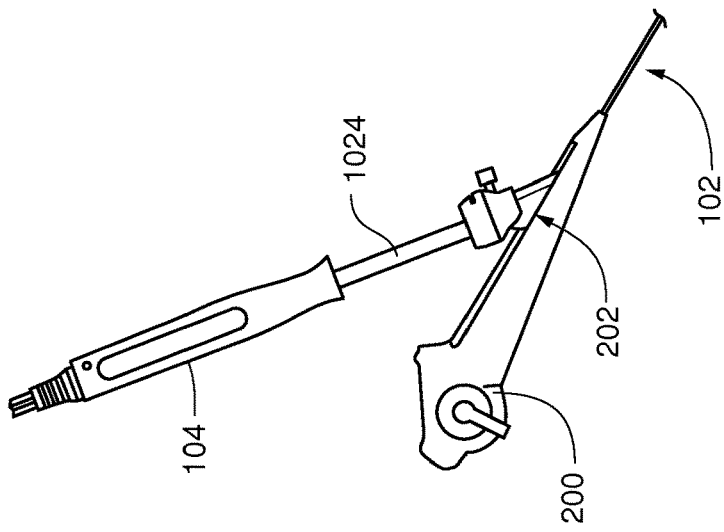

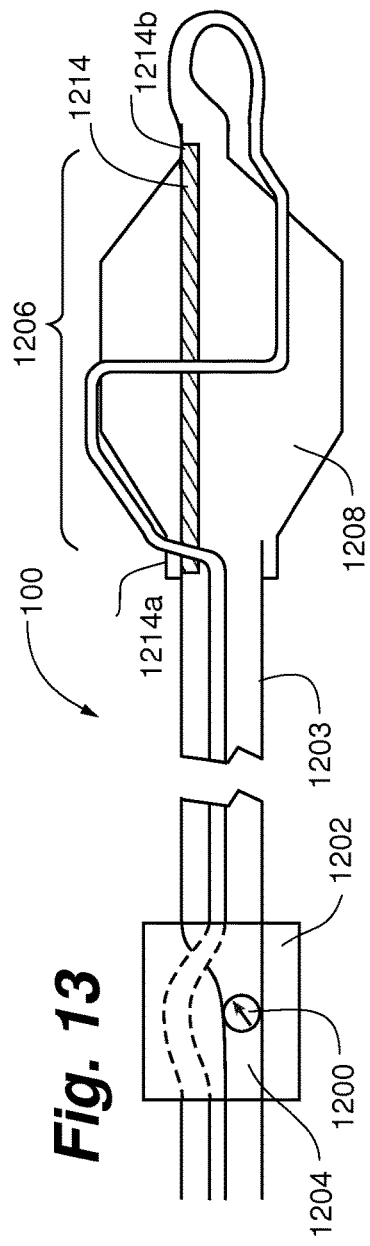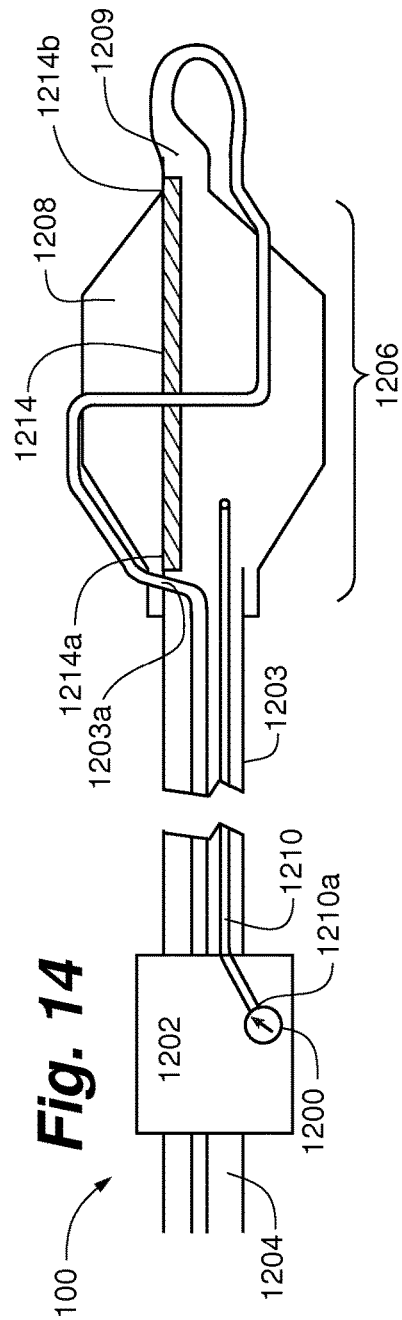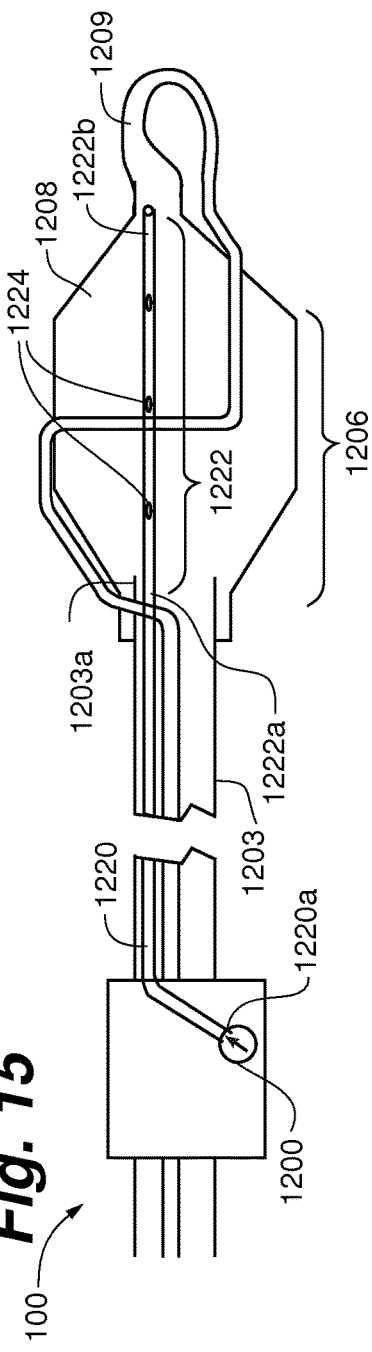

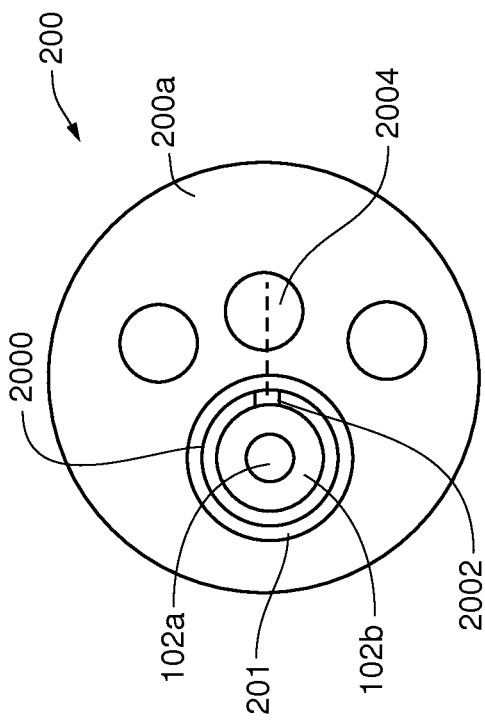

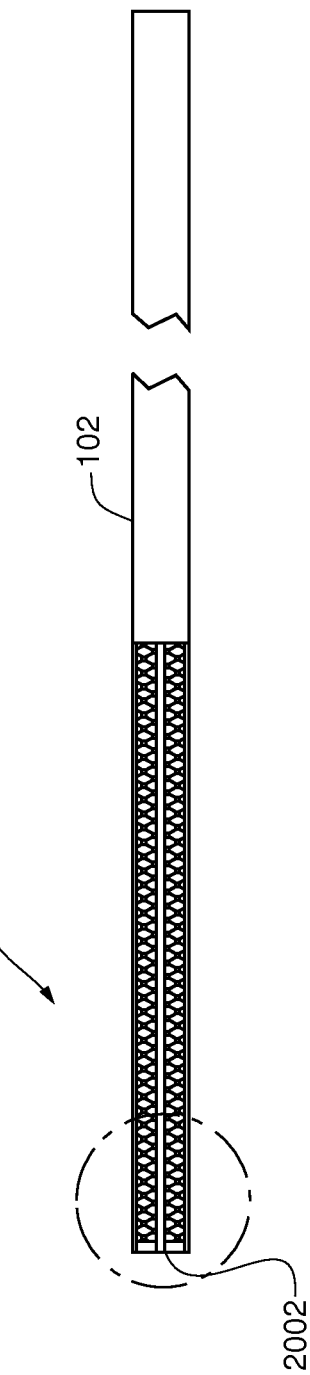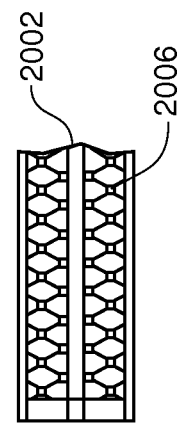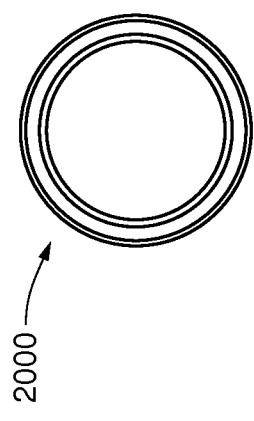
Fig. 17A
Fig. 17B
Fig. 17C

CATHETER AND HANDLE ASSEMBLY, SYSTEMS, AND METHODS

RELATED APPLICATION

The present application is a National Phase entry of PCT Application No. PCT/US2014/069971 filed Dec. 12, 2014 which claims the benefit of U.S. Provisional Application No. 61/915,282 filed Dec. 12, 2013, which is incorporated herein in its entirety by reference.

TECHNICAL FIELD

The present invention relates generally to systems, apparatuses, and methods for treating tissue, and more particularly, the invention relates to a catheter and handle system including a catheter positioning handle assembly that facilitates both circumferential and axial positioning of a distal end of the catheter positioned in an airway, conduit, or vessel.

BACKGROUND

Pulmonary diseases are some of the most common medical conditions, affecting tens of millions of people in the U.S. alone. Pulmonary diseases result from problems in the respiratory tract that interfere with proper respiration. Many of these diseases require medical attention or intervention in order to restore proper lung function and improve a patient's overall quality of life. Some of the more common pulmonary diseases include asthma and chronic obstructive pulmonary disease or COPD. Symptoms of pulmonary disease like COPD and asthma vary but often include a persistent cough, shortness of breath, wheezing, chest tightness, and breathlessness. Generally, these symptoms are exacerbated when performing somewhat strenuous activities, such as running, jogging, brisk walking, etc. However, these symptoms may be noticed when performing non-strenuous activities, if the disease is allowed to progress unchecked. Over time, especially if medical attention is not sought, a person's daily activities will be significantly impaired, thus reducing overall quality of life.

Many pulmonary diseases, whether acute or chronic, often involve pathologic conditions associated with airway inflammation. When such inflammation has developed at the airway, infiltrated inflammatory cells cause damage to bronchial or lung tissue, which eventually results in the respiratory dysfunction characteristic of pulmonary diseases, such as reduction in respiratory flow rate or oxygen exchange capacity. Over time, this inflammation can lead to blockage of the airway lumen, thickening of the airway wall, and alteration of structures within or around the airway wall. Airway obstruction can significantly decrease the amount of gas exchanged in the lungs resulting in breathlessness. Blockage of an airway lumen can be caused by excessive intraluminal mucus, edema fluid, or both. Thickening of the airway wall may be attributable to excessive contraction of the airway smooth muscle, airway smooth muscle hypertrophy, mucous glands hypertrophy, inflammation, edema, or combinations of these. Alteration of structures around the airway, such as destruction of the lung tissue itself, can lead to a loss of circumferential traction on the airway wall and subsequent narrowing of the airway. Generally, pulmonary diseases like COPD and asthma are the result of a complex interplay of local inflammatory cytokines, inhaled irritants (e.g., cold air, smoke, allergens, or other chemicals), systemic hormones (e.g., cortisol and epinephrine), local nervous system input (i.e., nerve cells contained completely within the airway wall that can produce local reflex stimulation of smooth muscle cells and mucous glands), and the central nervous system input (i.e., nervous system signals from the brain to smooth muscle cells and mucous glands carried through the vagus nerve).

Asthma can further include acute episodes or attacks of additional airway narrowing via contraction of hyper-responsive airway smooth muscle that significantly increases airflow resistance. Asthma symptoms include recurrent episodes of breathlessness (e.g., shortness of breath or dyspnea), wheezing, chest tightness, and coughing. Additionally, COPD, often referred to as emphysema, is characterized by the alteration of lung tissue surrounding or adjacent to the airways in the lungs. Emphysema can involve destruction of lung tissue (e.g., alveolar sacs) that leads to reduced gas exchange and reduced circumferential traction applied to the airway wall by the surrounding lung tissue. The destruction of alveoli tissue restricts the in-flow of oxygen rich air and the proper function of healthier tissue, resulting in significant breathlessness. Exposure to chemicals or other substances (e.g., tobacco smoke) may significantly accelerate the rate of tissue damage or destruction. Additionally, chronic bronchitis, another type of COPD, is characterized by contraction of the airway smooth muscle, smooth muscle hypertrophy, excessive mucus production, mucous gland hypertrophy, and inflammation of airway walls. Like asthma, these abnormalities are the result of a complex interplay of local inflammatory cytokines, inhaled irritants, systemic hormones, local nervous system, and the central nervous system. Unlike asthma where respiratory obstruction may be largely reversible, the airway obstruction in chronic bronchitis is primarily chronic and permanent.

Treatment for pulmonary diseases includes reducing exposure to harmful agents, administering medications (e.g., bronchodilators, steroids, phosphodiesterase inhibitors, theophylline, antibiotics, etc.), administering lung therapy (e.g., oxygen therapy, pulmonary rehabilitation), and surgical intervention, such as bronchial thermoplasty. Unfortunately, pharmacological treatment requires patient compliance, often causes harmful side effects, and does not necessarily treat the underlying cause of the disease. Similarly, surgical intervention can result in the destruction of smooth muscle tone and nerve function, such that the patient is unable to respond favorably to inhaled irritants, systemic hormones, and both local and central nervous system input.

An alternative method for treating pulmonary disease is referred to as targeted lung denervation. This method utilizes ablation, such as RF ablation, via an ablation assembly to selectively treat target regions inside of the airway wall (e.g., anatomical features in the stromas) while protecting the superficial tissues, such as the surface of the airway wall. For example, the mucous glands can be damaged to reduce mucus production a sufficient amount to prevent the accumulation of mucus that causes increased air flow resistance while preserving enough mucus production to maintain effective mucociliary transport, if needed or desired. Nerve branches/fibers passing through the airway wall or other anatomical features in the airway wall can also be destroyed.

Specially designed catheters allow for the introduction of an ablation assembly, generally comprising one or more collapsible electrodes or energy emitters, coupled to an expandable member, such as a balloon, into the airway of a patient via a delivery device. The delivery device can be a guide tube, a delivery sheath, a bronchoscope, or an endoscope and can include one or more viewing devices, such as optical viewing devices (e.g., cameras), optical trains (e.g., a set of lens), optical fibers, CCD chips, and the like. Once positioned in the desired region of the airway, such as the left and/or right main bronchi, the expandable member is expanded to position the one or more electrodes in contact with the airway wall.

Energy, such as RF energy, is supplied to the energy emitter to ablate the targeted tissue, causing a lesion to form, therefore temporarily or permanently damaging the targeted tissue, therefore affecting, e.g. attenuating nerve signals to or from, portions of the lungs associated with the targeted tissue. Simultaneously, a coolant is supplied through the catheter and is directed to the one or more electrodes and into the expandable member or balloon. This allows for cooling of the superficial tissue in contact with the electrode, as well as the adjacent tissues. The size, shape, and depth of the lesions are determined by the flow rate and temperature of the coolant, and the energy supplied to the energy emitter(s). Devices, systems, and methods of such procedures can be found, for example, in one or more of U.S. Pat. No. 8,088,127 entitled "Systems, Assemblies, and Methods for Treating a Bronchial Tree," and U.S. Patent Application Publication No. 2011/0152855 entitled "Delivery Devices with Coolable Energy Emitting Assemblies," both of which are incorporated herein by reference in their entireties.

In order to ensure that most or all of the target nerves extending along the airway are treated, it is generally desirable to form a circumferential lesion around all or most of the circumference of the airway wall. Due to design constraints or preferences, the electrode or energy emitter may not extend around the entirety of the circumference of the airway wall. Therefore, a circumferential lesion may be formed by ablating tissue while slowly rotating the ablation assembly or by positioning the ablation assembly in a series of rotational positions at each of which energy is delivered for a desired time period. The adjacent lesions then become contiguous and form a circumferential band all the way around the airway wall. Additionally or alternatively, the catheter may be repositioned axially to treat other locations within the airway distally or proximally of the first treatment site.

Typically targeted lung denervation will be performed under bronchoscopic visualization. A bronchoscope may be introduced into the target airway and the treatment catheter then delivered either alongside the bronchoscope or, more preferably, through the working channel of the bronchoscope. However, placement through the working channel can create challenges in manipulating the catheter due to the small size of the working channel, friction between the catheter and the walls of the working channel, and, in the case of flexible bronchoscopes, the curvature or tortuosity of the working channel. Furthermore, it is easy to lose the relative position of the electrode from the camera if both can rotate independently because the camera will always project right side up in the airway, regardless of the position of the bronchoscope.

Disorientation of the electrode in the treatment site and/or unintended movement of the catheter relative to the bronchoscope during treatment may result in treatment inaccuracies, causing axial or circumferential misalignment of lesions, undesirable gaps between lesions, or excessive overlap between lesions.

To address these and other challenges, there remains a need for a system, device, or apparatus for precise positioning and manipulation of pulmonary treatment catheters, such as targeted lung denervation catheters, while easily maintaining electrode orientation when positioned in a pulmonary airway through a delivery device such as the working channel of bronchoscope.

SUMMARY

Embodiments of the invention are directed to a pulmonary treatment catheter and handle system including a catheter assembly, a handle assembly, and a scope coupling assembly for coupling the handle assembly and catheter assembly to a delivery device, such as a bronchoscope. Embodiments are further directed to kit including the catheter assembly and handle assembly for coupling together and to a delivery device, such as a bronchoscope, via the scope coupling assembly, and instructions for methods of using such. The catheter assembly is further fluidly and electrically coupled to a system console, including a coolant supply and return reservoir, and an energy supply such as a RF generator, via the handle assembly.

The catheter assembly, handle assembly, and scope coupling assembly cooperate together to facilitate both circumferential and axial positioning of a catheter electrode in a treatment site, such as an airway, conduit, or vessel for treatment of the tissue, while maintaining known rotational and axial orientation of portions of the catheter assembly, such as an ablation assembly including an energy emitter or electrode, within the treatment site. The system can further facilitate optical coupling of the ablation assembly of the catheter assembly with a viewing device, such as a fiber optic camera at a working end of a bronchoscope, while maintaining independent movement of the viewing device with respect to the ablation assembly to achieve maximum viewing flexibility of the treatment site and ablation assembly. This allows for full viewing access of the electrode of the ablation assembly within the treatment site regardless of its or orientation or positioning within the treatment site.

In embodiments, the catheter assembly comprises a targeted lung denervation RF, microwave, or ultrasound catheter, and generally includes an elongate shaft, and an ablation assembly coupled to a distal portion of the shaft, the ablation assembly including an expandable member, such as a balloon or basket, and one or more electrodes or energy emitters coupled to the expandable member. The catheter assembly also includes a cooling circuit including a coolant inflow and outflow lumen within the elongate shaft, and a coolant inlet path and return path (e.g. cooling conduit(s)) to circulate coolant to the expandable member and to the energy emitter, one or more power wires for supplying power to the energy emitter, optional thermocouple(s) and associated wires for measuring and sensing temperature at locations proximal to the electrode, optional cooling circuit pressure sensors and associated wired for measuring and sensing pressure within the cooling circuit, and/or optional pressure relief valves.

In embodiments, the handle assembly is coupled to a proximal portion of the shaft. The handle assembly can include a housing fixedly coupled to the proximal end of the shaft, and a spindle tube or handle frame coupled to the housing such that the spindle tube is rotatably and axially shiftable with respect to the housing and the catheter assembly. The handle assembly can further include an umbilical cable with strain relief for coupling the handle assembly, and ultimately the catheter assembly, to a system console including a heat exchanger, coolant pump, energy generator (such as an RF, microwave, or ultrasound generator), and a system controller. The umbilical cable can aid in coupling, for example, inlet and return fluid tubes (coolant) from the system console for fluidly coupling the catheter assembly to the heat exchanger and pump of the console, an electrical cable/connector to electrically connect the electrode of the catheter assembly to an energy source, thermocouple wires to monitor temperature of the surface tissue of the treatment site, the electrode, or both, and/or pressure sensors to monitor the high pressure coolant inlet flow and the low pressure return flow.

In embodiments, the scope coupling assembly removably couples the handle assembly and catheter assembly to a working channel of a delivery device, such as a bronchoscope, in a unique or single orientation, such that the initial rotational and axial orientation of the catheter assembly with respect to the working end or tip of the bronchoscope is known. The coupling assembly is fixedly coupled to the spindle tube, such that the handle housing and catheter assembly are rotatably and axially shiftable with respect to the working channel.

In some embodiments, the handle assembly is configured to maneuver the distal portion of the catheter shaft having the ablation assembly thereon with respect to the delivery device and airway wall, in axial and circumferential directions during or in preparation for the administration of treatment for a pulmonary disease. In some aspects, the delivery device is a bronchoscope that comprises a working channel or port through which the elongate shaft and ablation assembly of the catheter can be inserted, and the handle assembly can be secured to the bronchoscope in a manner that functionally engages the handle assembly movements with the bronchoscope and the ablation assembly of the catheter assembly. For example, the handle assembly can be fixed to the bronchoscope such that the shaft of the catheter assembly, and therefore the ablation assembly, rotates and axially translates with corresponding rotational and axial translation of the bronchoscope for coarse adjustment of the ablation assembly within the airway. The handle assembly may also include one or more steering or manipulation mechanisms that are functionally coupled with the shaft and/or ablation assembly to translate the shaft and/or ablation assembly rotationally and/or axially with respect to the scope for either coarse or fine circumferential and/or axial adjustment while other portions of the handle assembly remain engaged with and stationary relative to the bronchoscope.

In a particular embodiment, a length of the elongate shaft of the catheter assembly and the manipulation mechanism of the handle assembly are configured to allow for a travel length of the ablation assembly to be equal to or greater than a longitudinal length of the ablation assembly such that an axial stroke of the handle assembly (fully retracted to fully extended) allows the ablation assembly to shift between being fully extended out of the working end or tip (with or without a gap outside of the working end) of the bronchoscope to fully retracted within the working end of the bronchoscope (with or without a gap inside of the working end).

In some embodiments, once engaged with the bronchoscope, a user can maneuver the bronchoscope, and the elongate shaft and ablation assembly thereon, into a position advantageous for conducting treatment for a pulmonary disease (e.g., a targeted lung denervation procedure). In some embodiments, the handle assembly can comprise controls for independently adjusting the distal portion of the elongate shaft of the catheter and/or the ablation assembly from the bronchoscope. In yet another embodiment, the handle assembly can comprise independent control mechanisms for axial translation of the catheter assembly and rotational movement of the catheter assembly with respect to the working channel of the bronchoscope.

In use, the handle is permanently or temporarily coupled to the catheter assembly, and the distal portion of the catheter shaft and ablation assembly are inserted into the working channel or port of a delivery device, such as a bronchoscope. The handle assembly is then coupled to the bronchoscope via the coupling assembly in a unique orientation. In some embodiments, the distal portion of the delivery device can comprise a visualization device, a camera, and/or an aspiration lumen or vacuum. In some embodiments, the distal end of the catheter shaft and ablation assembly can be positioned using the axial and circumferential controls of the handle assembly, such that a specific portion of airway tissue can be targeted for treatment (e.g., radio frequency energy emission from an electrode). In embodiments, the working end of bronchoscope can be maneuvered independently of the catheter shaft and ablation assembly. For example, the handle assembly can be used to more accurately position an electrode of the ablation assembly based on visual cues from the camera of the delivery device, without moving the delivery device and camera.

In embodiments, the distal end of the catheter assembly includes a longitudinal indicator band or stripe. When the catheter assembly and handle assembly are coupled to the working channel of the bronchoscope, the indicator band aligns with the center point of the camera of the bronchoscope. This band provides a visual confirmation of the ablation assembly orientation within the treatment site, and regardless of the rotational orientation of the bronchoscope within the treatment site, the location of the ablation assembly with respect to the working end of the bronchoscope is known. Furthermore, the band provides a visual confirmation of the axial location of the ablation assembly with respect to the working end of the bronchoscope to provide optimal optical coupling of the bronchoscope camera and the ablation assembly.

The system according to embodiments allows for one-handed operation of both the catheter assembly and the bronchoscope when rotated and/or translated axially together for coarse adjustment, as well as for the independent rotationally and axial fine adjustment of the ablation assembly with respect to the bronchoscope.

The above summary of the various representative embodiments of the invention is not intended to describe each illustrated embodiment or every implementation of the invention. Rather, the embodiments are chosen and described so that others skilled in the art can appreciate and understand the principles and practices of the invention. The figures in the detailed description that follow more particularly exemplify these embodiments.

BRIEF DESCRIPTION OF THE DRAWINGS

The invention can be more completely understood in consideration of the following detailed description of various embodiments of the invention in connection with the accompanying drawings, in which:

FIG. 1 is an illustration of a pulmonary treatment catheter and handle system including a catheter assembly having an elongate shaft and an ablation assembly coupled to one end of the shaft, and a handle assembly coupled to the other end of the shaft, according to an embodiment.

FIG. 2 is a top view of a pulmonary treatment catheter and handle system including a catheter assembly having an elongate shaft and an ablation assembly coupled to one end of the shaft, and a handle assembly coupled to the other end of the shaft, according to an embodiment.

FIG. 3 is an illustration of an ablation assembly coupled to the distal portion of the elongate shaft of the catheter according to an embodiment.

FIG. 5 is an illustration of three positions of a catheter and handle assembly coupled to a delivery device according to an embodiment.

FIG. 13 is a cross-sectional side elevational view of a catheter and handle system with a pressure monitoring assembly according to an embodiment.

FIG. 14 is a cross-sectional side elevational view of a catheter and handle system with a pressure monitoring assembly according to an alternative embodiment.

FIG. 15 is a cross-sectional side elevational view of a catheter and handle system with a pressure monitoring assembly according to another alternative embodiment.

FIG. 16 is an end view of a working end of a bronchoscope with catheter extending through a working channel according to an embodiment.

FIG. 17A-C is an elevational, cross-sectional, and exploded illustration of a distal end of an elongate shaft of a catheter assembly having an orientation indicator thereon.

DETAILED DESCRIPTION

Figure 4:
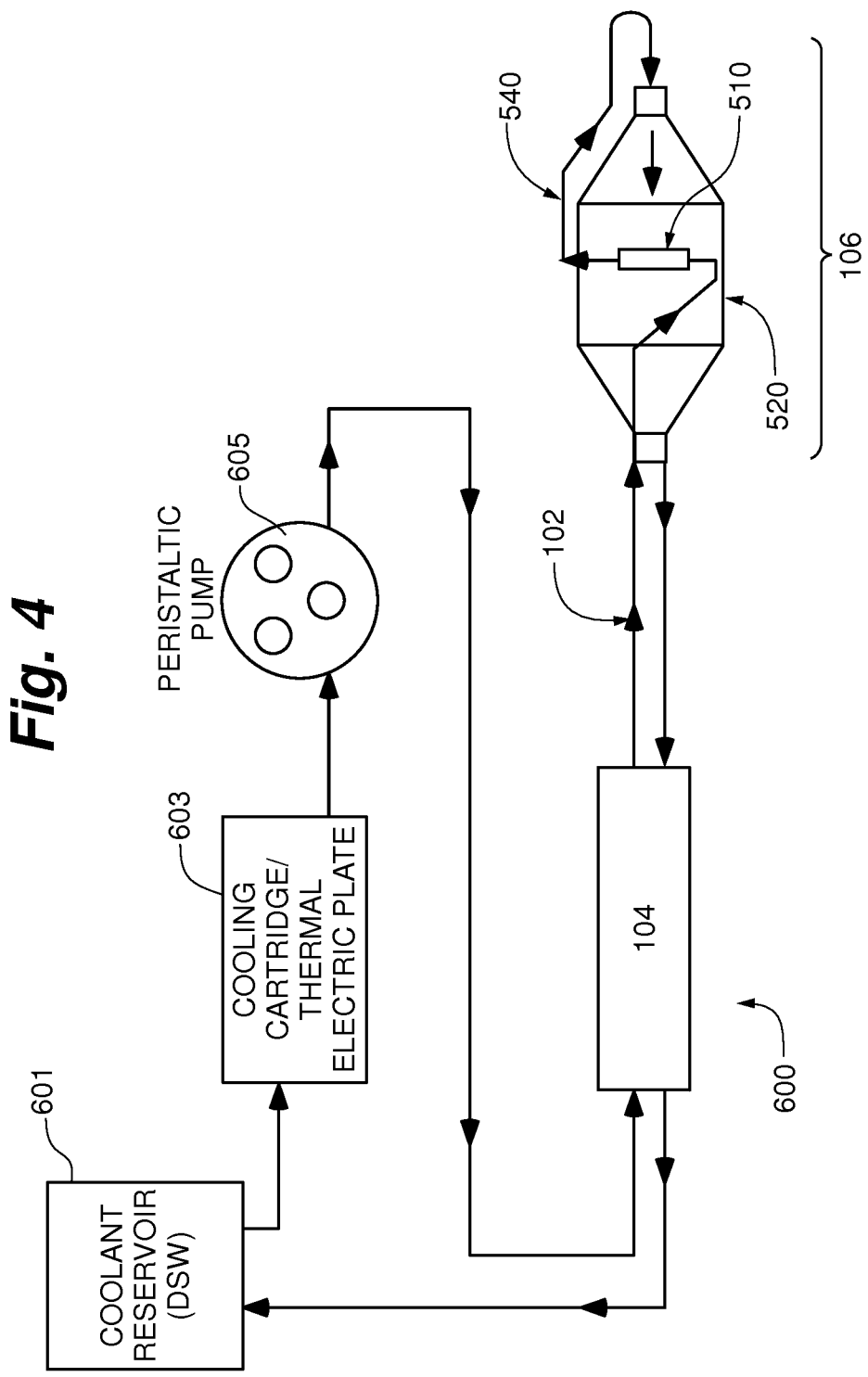
FIG. 4 is a diagram illustrating the direction of fluid flow in a cooling circuit according an embodiment.

As illustrated in FIGS. 1 and 2, a catheter and handle system 100 according to an embodiment of the present invention can comprise an ablation catheter assembly 101 having an elongate shaft 102 and an ablation assembly 106 coupled to a first or distal end of shaft 102, a positioning handle assembly 104 coupled to a second or proximal end of shaft 102, and a scope coupling assembly 103 for coupling catheter assembly 101 and handle assembly 104 to a working channel of a delivery device, such as a bronchoscope. Catheter assembly 101 is further fluidly and electrically coupled to a system console (not shown), including a coolant supply and return reservoir, and an energy supply such as a RF generator, via handle assembly 104. Handle assembly 104 is configured to maneuver the distal portion or end of shaft 102 and therefore ablation assembly 106 in axial and circumferential directions during the administration of treatment.

As shown in FIG. 3, in one non-limiting embodiment of the invention, ablation assembly 106 can comprise one or more energy emitters 510, such as an electrode, and an expandable member 520, such as a balloon or basket. In some embodiments, ablation assembly 106 can comprise a coolant fluid path or cooling circuit 600 to cool electrode 510 and a surface of expandable member 520 to protect surface tissue in contact with electrode 510 and adjacent to electrode 510. As depicted in FIG. 4, cooling circuit 600 includes coolant supplied from a reservoir 601 of a system console, through an optional heat exchanger 603 of the system console, through handle 104, through an inflow lumen in shaft 102, through conduit 540 to which electrode 510 is coupled, through expandable member 520, through an outflow lumen in shaft 102, through handle 104, and back to the system console. Non-limiting examples of a system console can be found in U.S. Patent Application Publication No. 2013/0289556, entitled "Delivery Devices with Coolable Energy Emitting Assemblies" and U.S. Pat. No. 8,489,192 entitled "System and Method for Bronchial Dilation," both of which are incorporated by reference in their entireties. Cycling of the fluid is accomplished, for example, by a peristaltic pump 605. In an alternative embodiment, the flow is reversed such that the coolant flows through the expandable member before the electrode.

Referring back to FIG. 3, ablation assembly 106 can optionally comprise a throttle valve 530 for regulating the flow between conduit 540 and expandable member 520. Ablation assembly 106 can also optionally comprise a support wire 1214, such as a Nitonol wire, extends along at least a length of catheter shaft 102 and between an interior of a proximal end 520a and distal end 520b of expandable member 520 to provide added axial, torsional, and buckling support for expandable member 520 and catheter shaft 102. More particularly, a first portion or end of 1214a of support wire 1214 is coupled to the distal end 102a of catheter shaft 102, while a second end 1214b is coupled to the distal end 520b of expandable member 520 at a junction between throttle value 530 and expandable member 520.

Further details of the ablation assembly are described in U.S. Pat. No. 8,088,127 entitled "Systems, Assemblies, and Methods for Treating a Bronchial Tree," and U.S. Patent Application Publication No. 2011/0152855 entitled "Delivery Devices with Coolable Energy Emitting Assemblies," both of which were incorporated by reference in their entireties above.

In some embodiments, and referring back to FIGS. 1 and 2, handle assembly 104 can comprise an umbilical cable 120 coupled to an end of handle assembly 104 via strain relief 121 for fluidly and/or electrically coupling catheter assembly 101 to accompanying devices or accessories, such as a power source, energy source, fluid or coolant supply, heat exchanger, and controller, preferably combined in a system console. Umbilical cable 120 can include, for example, connections for inlet and return fluid tubes or lumens 105 for fluidly coupling shaft 102 to a fluid or coolant supply, from the console which optionally includes a heat exchanger for cooling and/or heating input fluid, and one or more electrical cable/connector 107 to electrically connect the shaft and/or ablation assembly to a power source, thermocouples for temperature monitoring, and/or pressure sensors for coolant circuit pressures. In other embodiments, handle assembly 104 can comprise an internal battery source for operating handle assembly 104 and any accompanying devices or accessories.

Referring to FIG. 5, catheter assembly 101 and handle assembly 104 are capable of coupling to a delivery device 200, such as, for example, a guide tube, a delivery sheath, a bronchoscope, or an endoscope. Delivery device 200 can include one or more viewing devices, such as optical viewing devices (e.g., cameras), optical trains (e.g., a set of lens), and the like. In one particular embodiment, delivery device 200 comprises a flexible bronchoscope. Ablation assembly (not shown) and elongate shaft 102 are inserted into a working channel port 202 of device 200. Handle assembly 104 is then secured to device 200 via a scope coupling assembly 103. Scope coupling assembly 103 can be integral with or coupled to handle assembly 104, or can be its own stand-alone adapter coupling to both handle assembly 104 and port 202. Scope coupling assembly 103 securely fits to port 202, such as by frictional or abutting fit, locking lever, threaded engagement of corresponding threads, bayonet or snap fit, spring loaded fit, or any of a variety of mechanisms known to those skilled in the art. Scope coupling assembly 103 further can include a locking mechanism 208 such as a lever or slide lock to prevent unintended disengagement of handle assembly 104 from port 202. Once secured, scope coupling assembly 103 is fixed axially and rotationally with respect to device 200. If not previously assembled, handle assembly 104 is then secured to scope coupling assembly 103, as will be described in more detail below.

Figure 6:
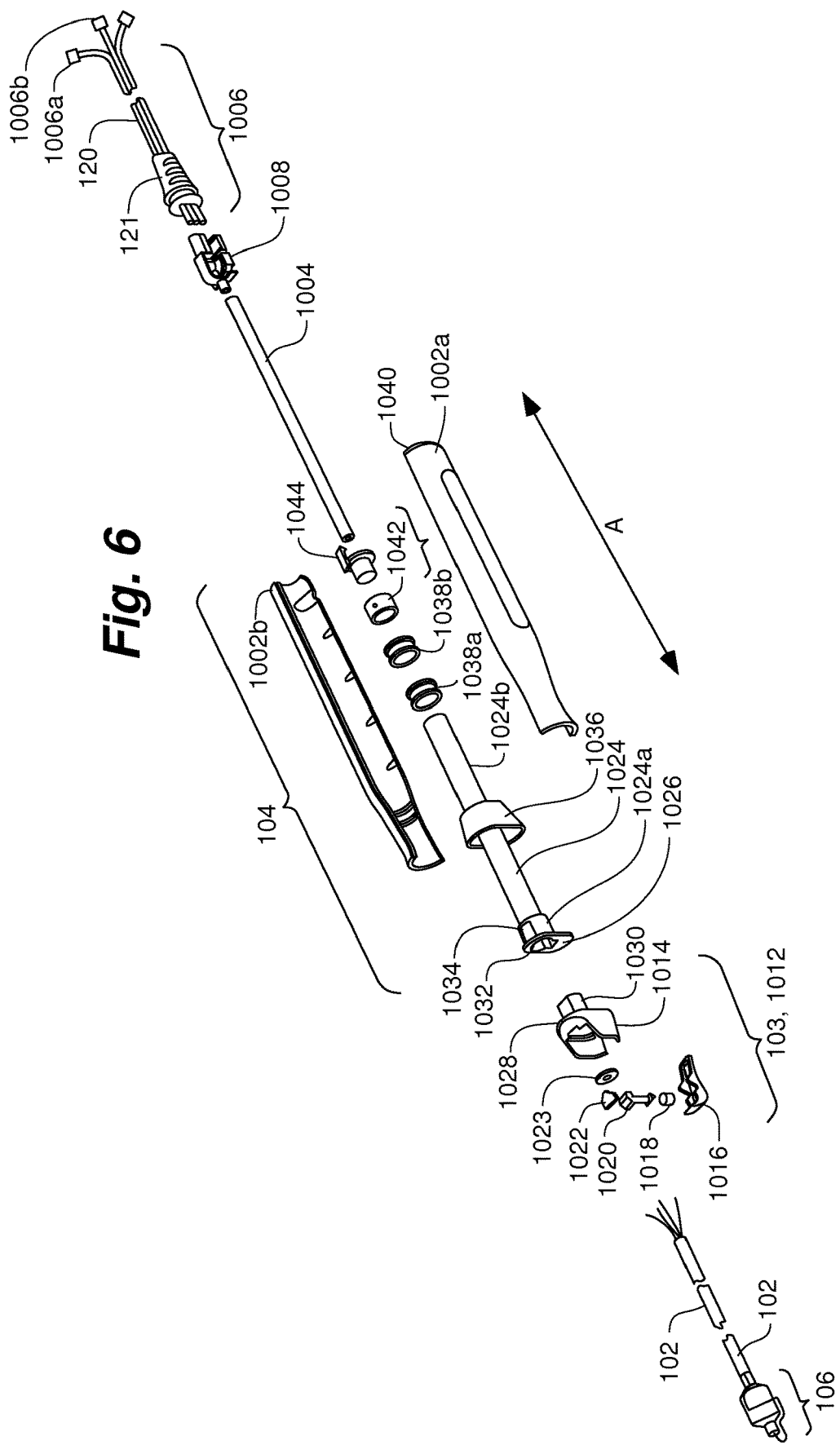
FIG. 6 is an exploded view of a handle assembly and coupling assembly according to an embodiment.
Figure 7:
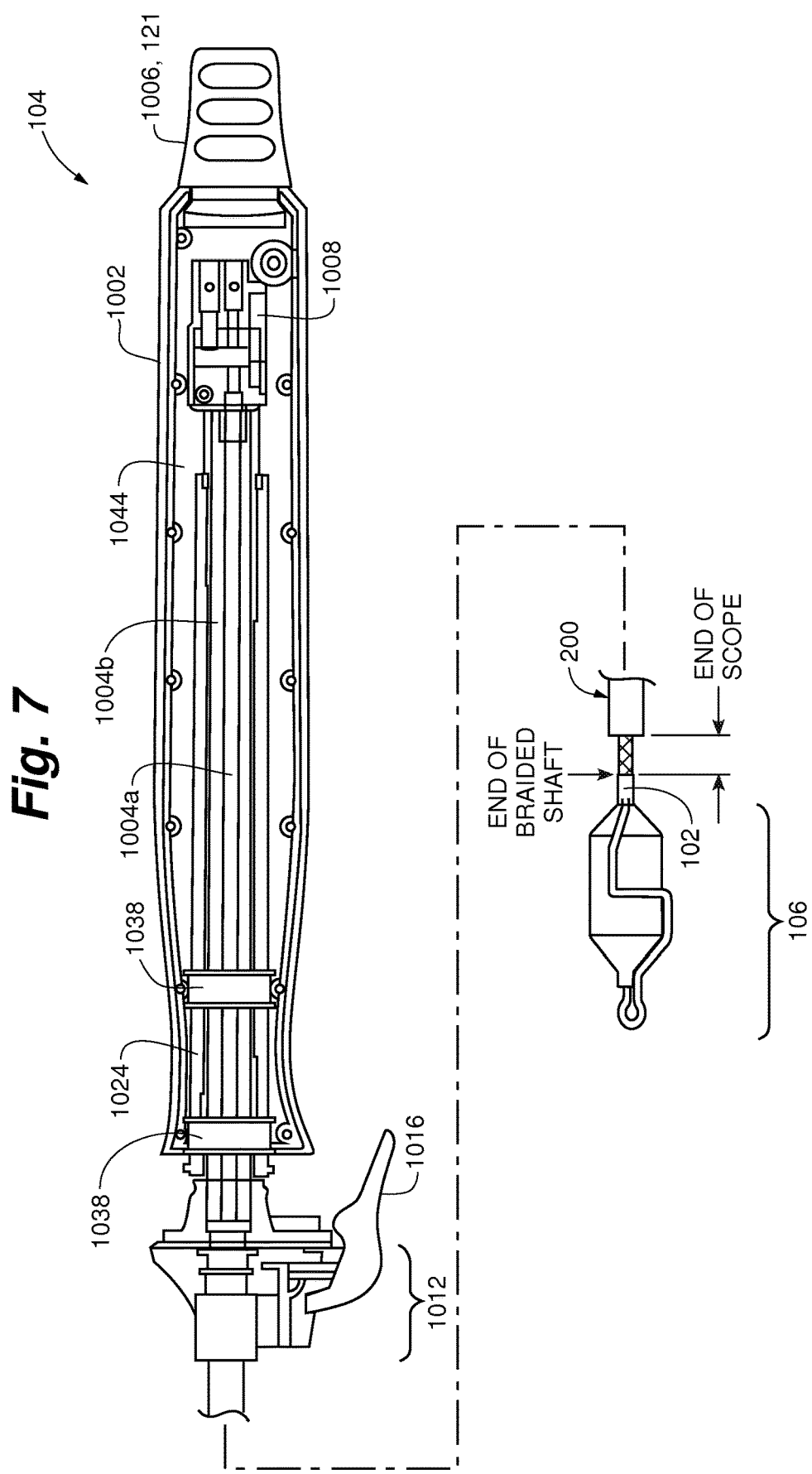
FIG. 7 is a partial cutaway view of the handle assembly of FIG. 4 in a retracted or closed configuration.

In a particular embodiment of handle assembly 104 and referring to FIGS. 6 and 7, handle assembly 104 generally comprises a handle housing or cover 1002 thereby defining an interior space of handle assembly 104 having a longitudinal axis A, and a handle frame, such as a spindle tube 1024. In an embodiment, housing 1002 comprises a first handle housing 1002a and second handle housing 1002b coupled to first handle housing 1002a via one or more a mortise and tenon joints, corresponding male and female interlocking parts, screws, adhesive, welding, or any of a variety of mechanisms for joining the housings. In other embodiments not shown, the housing is monolithic, or alternatively, formed of more than two pieces.

Figure 8:
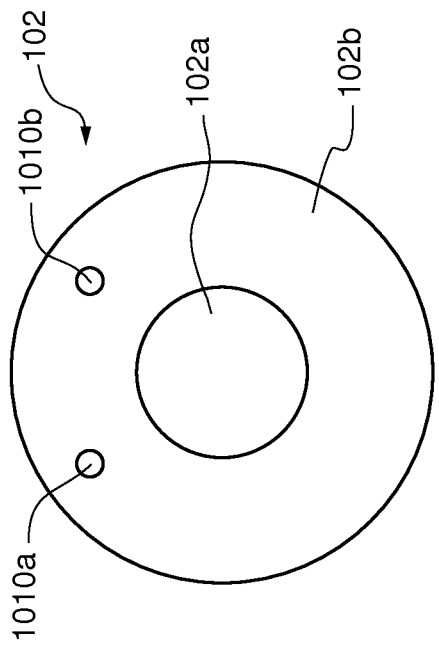
FIG. 8 is a cross-sectional view of an elongate shaft of a catheter according to an embodiment.

A portion of elongate shaft 102 of the catheter assembly 101, extends along longitudinal axis A within handle housing 1002. A catheter tube 1004 sheaths and protects shaft 102 within housing 1002. In an embodiment, and referring to FIG. 8, catheter shaft 102 includes a central coolant inlet lumen 102a for supplying fresh or recycled coolant from a coolant supply of the system console to the ablation assembly coupled to a distal end of catheter 102 (e.g. shown in FIG. 6). A coolant return lumen 102b surrounds coolant inlet lumen 102a such that the coolant return lumen 102b and coolant inlet lumen 102a are coaxial. However, other arrangements that are not coaxial, such as side-by-side, can also be contemplated.

Referring to FIG. 6, an umbilical cable assembly 1006 of handle assembly 104 at a proximal end couples coolant inlet lumen 102a and coolant return lumen 102b of shaft 102 to a coolant supply source and return reservoir. As explained previously with respect to FIGS. 1 and 2, umbilical cable assembly 1006 can couple any of a variety of tubes and/or electrical wires or cables to catheter tube 1004 and/or handle assembly 104 for fluidly and/or electrically coupling catheter shaft 102 and ultimately ablation assembly 106 to accompanying devices or accessories, such as a power source, energy source, fluid or coolant supply, heat exchanger, and controller, preferably combined in a system console. Preferably, umbilical cable assembly 1006 comprises flexible umbilical cable 120 terminating in a rubber strain relief 121.

Referring to FIGS. 9-12, catheter tube 1004 and the proximal end of shaft 102 are operably coupled to umbilical cable assembly 1006 via a manifold 1008. Manifold 1008 distributes or redirects the inflow, outflow, and/or electrical flows between shaft 102 and the system console (not shown).

Figure 11:
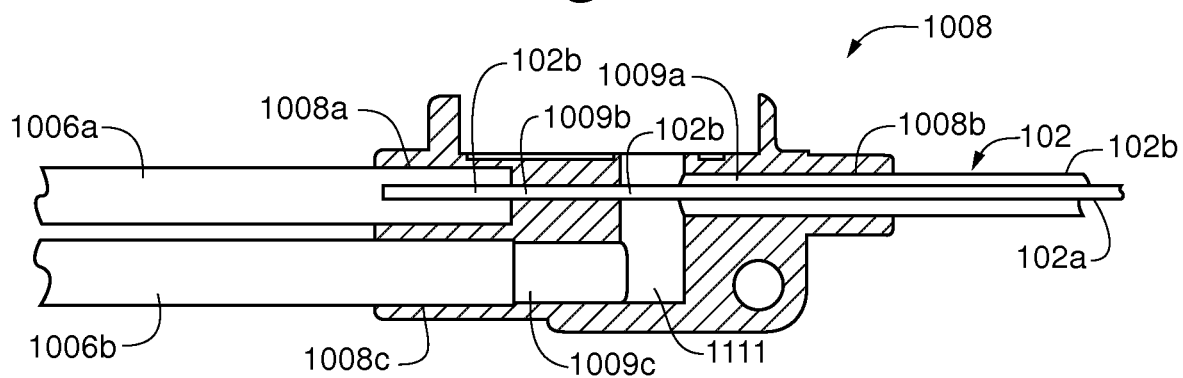
FIG. 11 is a cross-sectional side view of a manifold coupled to a catheter shaft and an umbilical cable according to an embodiment.
Figure 12:
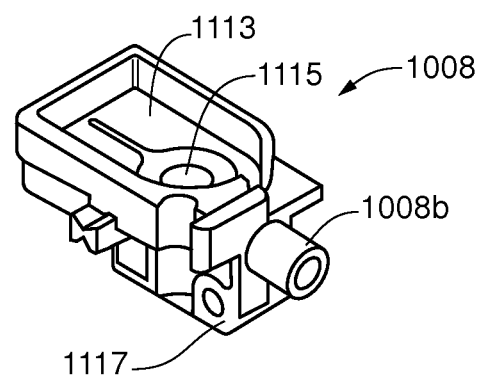
FIG. 12 is a perspective view of a manifold according to an embodiment.

In an embodiment, and referring to FIGS. 11 and 12, manifold 1008 comprises a first inlet port 1008a and a second inlet port 1008b. First inlet port 1008a and second inlet port 1008b are in fluid communication with each other via conduits 1009a and 1009b and gate 1111. A proximal end of coolant supply tube 1006a of umbilical cable assembly 1006 extends within and is bonded to an interior surface of first port 1008a of manifold 1008 by adhesive bonding, heat sealing, ultrasonic welding, or any of a variety of attachment mechanisms. A distal end (not shown) of coolant supply tube 1006a is coupled to a coolant supply, optional heat exchange, and pump of the system console.

Inlet lumen 102a and outlet lumen 102b of shaft 102 extends within second port 1008b of manifold 1008, and outlet lumen 102b is bonded to an interior surface of port 1008b by adhesive bonding, heat sealing, ultrasonic welding, or any of a variety of attachment mechanisms. Inlet lumen 102a extends beyond outlet lumen 102b of shaft 102 through conduits 1009a and 1009b, and into coolant supply tube 1006a. Optionally, a diameter of conduit 1009b is similar to a diameter of inlet lumen 102a, such that inlet lumen 102a can be bonded to an interior surface of conduit 1009b by adhesive bonding, heat sealing, ultrasonic welding, or any of a variety of attachment mechanisms.

Manifold 1008 further comprises a third port 1008c. A proximal end of coolant return tube 1006b of umbilical cable assembly 1006 extends within port 1008c and is bonded to an interior surface of third port 1008c by adhesive bonding, heat sealing, ultrasonic welding, or any of a variety of attachment mechanisms. Third port 1008c is in fluid communication with second port 1008b, and therefore outlet lumen 102b secured thereto, via conduits 1009c and 1009a, separated by gate 1111. A distal end (not shown) of coolant return tube 1006b is coupled to a reservoir of the system console for recycle and/or disposal of coolant.

In use, coolant is supplied from the coolant supply of the system counsel through coolant supply tube 1006a of umbilical cable assembly 1006. Coolant then flows from coolant supply tube 1006a into inflow lumen 102a of catheter shaft 102. Coolant flows along the length of shaft 102 into ablation assembly 106, as described below. The coolant circulates through ablation assembly 106 and into outlet lumen 102b, along the length of shaft 102 into manifold conduit 1009a, reservoir, 1111, and conduit 1009c. Coolant flows out of manifold 1008 via coolant return tube 1006b and back to the system console for recycle and/or disposal.

Referring back to FIGS. 9 and 10, catheter tube 1004 is bonded to an exterior surface of second port 1008a of manifold 1008, thereby covering second port 1008a and the portion of shaft 102 extending within and along handle assembly 100. Catheter tube 1004 is secured to manifold 1008 by adhesive bonding, heat sealing, ultrasonic welding, or any of a variety of attachment mechanisms.

Figure 9:
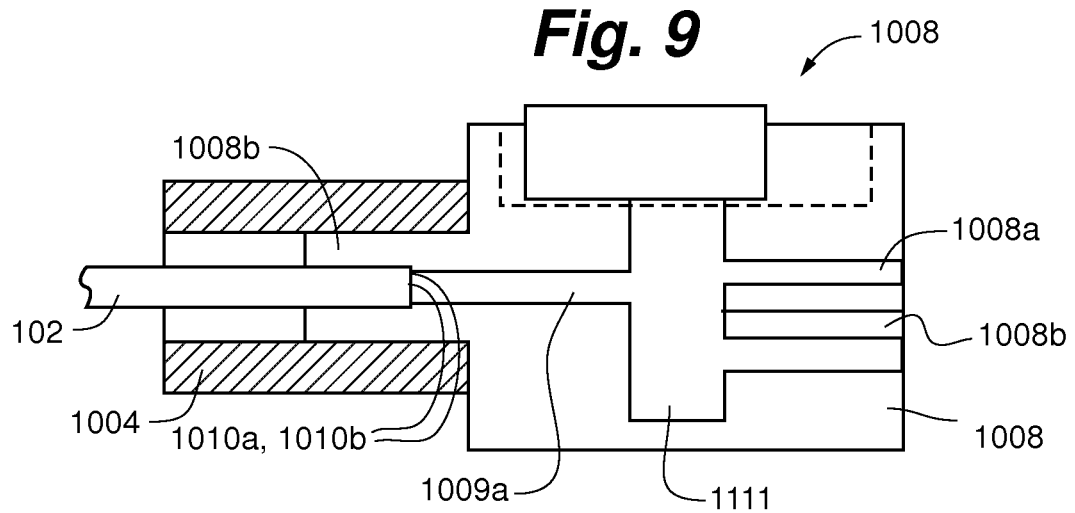
FIG. 9 is a cross-sectional side view of a manifold coupled to a catheter shaft, catheter tube, and an umbilical cable according to an embodiment.
Figure 10:
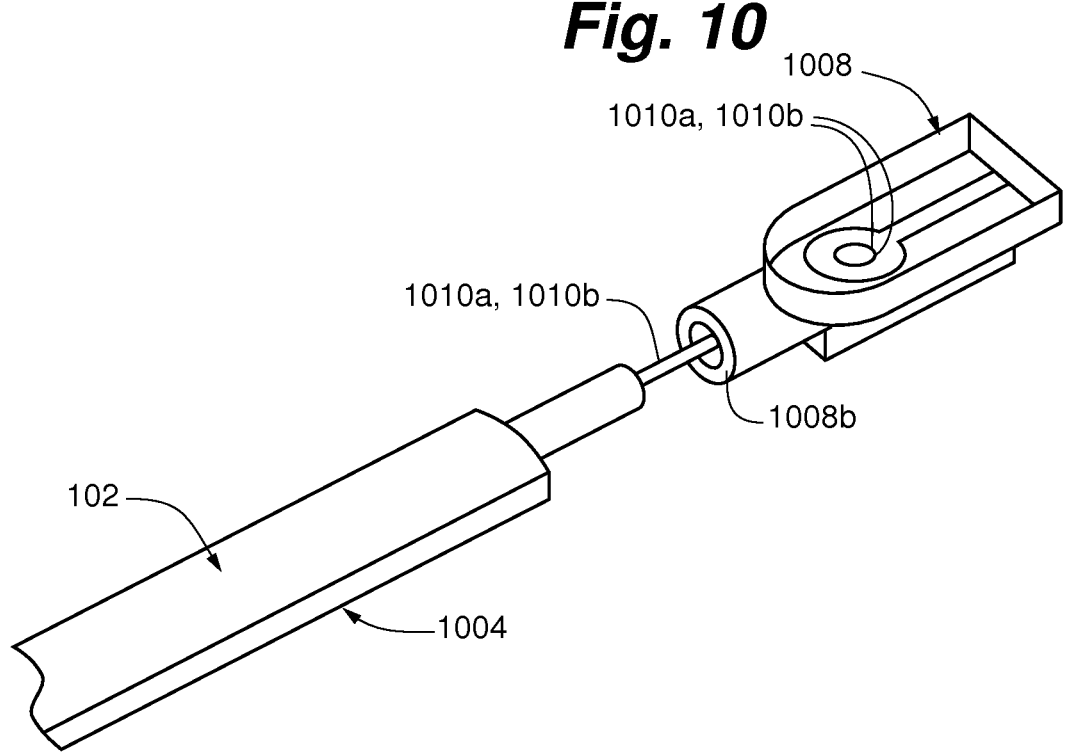
FIG. 10 is a perspective and partially exploded view of manifold and catheter shaft according to an embodiment of the invention.

Referring to FIGS. 9, 11, and 12, manifold 1008 can further comprise a recessed seat 1113 formed in a surface thereof for receiving and securing one or more printed circuit boards thereto, such as by soldering or additive printing directly thereon, and one or more liquid pressure sensors and gauges, flow sensors and gauges, and/or thermocouples for detecting and optionally displaying pressures, coolant inlet and outlet flow rates, and/or temperatures at various locations in the catheter assembly 101 and/or ablation assembly 106. Leads from the pressure sensor, flow sensors, and/or thermocouples are then fed through an aperture 1115 formed in seat 1113 of manifold 1008 which fluidly couples seat 1113 with gate 1111. The leads extend through shaft 102 to ultimately reach ablation assembly 106. In an embodiment, and referring back to FIG. 8, a first lead 1010a and a second lead 1010b are fed through outlet lumen 102b of shaft 102 to ablation assembly 106.

Manifold 1008 is fixedly coupled to an interior of first and/or second handle cover 1002a,b such that manifold 1008 and therefore catheter tube 1004 are fixed axially and rotationally to covering 1002. Manifold 1008 can be fixed to handle cover 1002a and/or 1002b by insertion of a peg formed on the interior of housing 1002a or b into a corresponding sleeve 1117 formed on manifold 1008 as seen in FIG. 12, for example. However, any of a variety of attachment mechanisms can be contemplated.

Thermocouples can be placed anywhere within the catheter assembly 101 including at the energy emitter or electrode site of the ablation assembly 106, within the cooling member of the ablation assembly to measure the temperature of the coolant in the cooling member, and/or within the inflow and/or outflow lumens 102a, 102b in the elongate shaft 102 to measure the temperatures of the inflow and/or outflow coolant flows. Coolant temperature and/or coolant flow are then either manually or automatically regulated at the system console to ensure that the ablation site is sufficiently heated to cause permanent damage to target tissue, while ensuring that surface tissue in contact with the electrode and cooling member is sufficiently cooled to inhibit or prevent permanent damage to the surface tissue.

Pressure and/or flow rate can be measured within the inflow and/or outflow lumens, and/or within the cooling member and/or ablation assembly to measure theoretical and/or direct pressure of the ablation assembly. Pressure within the inflow lumen can be high compared to pressure within the outflow lumen due to a throttle positioned within the ablation assembly. In a particular embodiment, a pressure of the expandable member, e.g. balloon, of the ablation assembly is held at a pressure less than a predetermined pressure to guard against over-dilating or over-sizing the balloon within the airway, which can cause unwanted damage to the airway. In the event that the inflow lumen, throttle, or outlet lumen gets clogged, a pressure sensor, such as one positioned on the handle, will detect the buildup of pressure in the corresponding line and will automatically trigger the coolant pump to shut off so as not to rupture the expandable cooling member or over-dilate the balloon, and/or the energy source for the electrode to shut off so that the treatment site does not overheat. In an alternative embodiment, pressure relief valves may be incorporated within the system to alleviate a buildup of pressure at a predetermined or user-controlled pressure limit. Specific pressure measurement assemblies are described in more detail below.

In one embodiment, and referring to FIG. 13, a pressure sensor 1200 is positioned on or near the handle assembly 1202 and is configured to measure the pressure of the outlet lumen 1204 of catheter shaft 1203. This embodiment is based on a pressure measurement downstream (i.e. the outlet lumen 1204) of the ablation assembly 1206, thereby requiring a theoretical pressure offset to estimate the pressure in the expandable member 1208 of the ablation assembly 1206. In this embodiment, it is estimated that a pressure in the expandable member 1208 is greater than a pressure at gauge 1200 due to the resistance of flow in the catheter shaft 1203 relative to the expandable member 1208.

In yet another embodiment of the invention, a direct measurement of the pressure in the balloon or ablation assembly 1206 is desired so as to eliminate or reduce undetected obstructions or occlusions between pressure sensor 1200 and the expandable member 1208, which can cause possible over-inflation or rupturing of the expandable member 1208. Referring to FIG. 14, a pressure sensor 1200 is positioned on or near the handle assembly 1202. A polymeric and/or metallic tube 1210 is positioned along outflow lumen 1204 of catheter shaft 1203. A first end 1210a of tube 1210 is operably coupled to the pressure sensor 1200 while a second end 1210b terminates within ablation assembly 1206. Tube 1210 acts as a static column to measure the pressure directly in ablation assembly 1206; i.e. the pressure through catheter shaft 1203 within tube 1210 is constant such that the pressure measured at pressure sensor 1200 is equal to the pressure in ablation assembly 1206.

In this embodiment, tube 1210 can be flexible or rigid. As seen in the figure, a support wire 1214, such as a Nitinol wire, extends between an interior of a proximal and distal end of expandable member 1208 to provide added axial, torsional, and buckling support for expandable member 1208. More particularly, a first end 1214a of support wire 1214 is coupled to the distal end 1203a of catheter shaft 1203, while a second end 1214b is coupled to the distal end of expandable member 1208 at a junction between throttle valve 1209 and expandable member 1208. In this embodiment, tube 1210 can supplement support wire 1214.

In yet another embodiment, and referring to FIG. 15, a pressure tube 1220 replaces the support wire of the previous embodiments. In this embodiment, tube 1220 is coupled at first end 1220a to pressure sensor 1200 positioned on or near the handle assembly 1202. A distal portion 1222 of tube 1220 extends between a proximal and distal end of expandable member 1208. More specifically, a proximal end 1222a of distal portion 1222 is coupled to the distal end 1203a of catheter shaft 1203, while a distal end 1222b of distal portion 1222 is coupled to the distal end of expandable member 1208 at a junction between throttle valve 1209 and expandable member 1208. Distal portion 1222 of tube 1220 includes one or more apertures 1224 positioned perpendicular to a longitudinal axis of tube 1220. Similar to the previous embodiment, tube 1210 acts as a static column to measure the pressure directly in ablation assembly 1206; i.e. the pressure through catheter shaft 1203 within tube 1210 is constant such that the pressure measured at pressure sensor 1200 is equal to the pressure in ablation assembly 1206. Furthermore, tube 1220 provides axial, torsional, and buckling support for the length of catheter shaft 1203 and expandable member 1208, allowing for thinner and more flexible fluid containment tubes (e.g. inflow and outflow lumens.

Process control loops including the real-time measurements of pressure, flow, and/or temperature within the system coupled with system response to automatically shut off provides a safety mechanism to guard against undesired tissue or airway injury.

Referring back to FIGS. 6 and 7, handle assembly 104 is releasably yet fixedly coupled to the working channel of a bronchoscope via a bronchoscope positioning assembly 1012. In an embodiment, positioning assembly 1012 comprises a scope coupler 1014 shaped so that it is mountable to the working channel in only a single rotational orientation. Scope coupler 1014 is coupled to the bronchoscope (or bronchoscope adapter assembly described below) via spring loaded jaw lever 1016, a jaw return spring (compression spring) 1018, sliding jaw 1020, stationary jaw 1022, and a silicone seal 1023 optionally bonded to either the stationary jaw 1022 or the coupler 1014. Force applied to lever 1016 extends spring 1018, thereby sliding jaw 1020 and jaw 1022 away from locking abutment with a recessed portion of the working channel to release scope coupler 1014 therefrom.

Spindle tube 1024 is fixedly coupled in both rotational and axial directions to scope coupler 1014 at a first end 1024a. More particularly, a flange or skirt 1026 of spindle tube 1024 abuts a flat surface 1028 of scope coupler 1014. A protrusion 1030 of scope coupler 1014 extends into an opening 1032 of spindle tube 1024, in a mortise and tenon fashion. A tab 1034 clicks into a portion of protrusion 1030 to lock scope coupler 1014 to spindle tube 1024. A spindle cover 1036 is coupled to handle cover 1002, such that spindle tube 1024 is axially slidable along its length through spindle cover 1036.

Spindle tube 1024 is axially extendable into and out of handle housing 1002 for fine axial adjustment via axial translation of handle housing 1002, and therefore manifold 1008 and catheter shaft 102, along longitudinal axis A with respect to spindle tube 1024. More particularly, spindle tube 1024 has an inner diameter larger than an outer diameter of catheter tube 1004 and therefore shaft 102, such that catheter tube 1004 and shaft 102 telescope axially within and out of spindle tube 1024 to achieve axial adjustment of ablation assembly 106. A length of travel of shaft 102 with respect to spindle tube 1024 is chosen based on a desired length of travel of ablation assembly 106 with respect to the working end or tip of the bronchoscope. In an embodiment, as handle housing 1002 extends axially away from scope coupler 1014, manifold 1008, being fixed to housing 1002, also extends away, pulling shaft 102 with it, thereby retracting the ablation assembly 106 coupled to a distal portion of the shaft 102 toward and optionally entirely or partly into the bronchoscope, and vice versa upon axial translation toward scope coupler 1014.

Handle housing 1002 and catheter tube 1004, and therefore shaft 102, are prevented from being completely pulled away from spindle tube 1024. More particularly, a second end 1024b of spindle tube 1024 is axially retained within housing 1002 via a spindle retainer assembly 1040. Spindle retainer assembly 1040 includes a spindle end cap 1042 affixed to an end of spindle tube 1024, and a handle stop 1044 coupled to spindle end cap 1042 via a U-shaped pin. As handle housing 1002 is axially extended from scope coupler 1014, in its full extension, radial protrusions of handle stop 1044 abut radially extending features protruding from an interior surface of handle housing 1002, thereby prohibiting further axial extension. Similarly, features on an interior surface of handle housing 1002 along the longitudinal length of housing 1002 about radially extending protrusions on an exterior surface of handle stop 1044 to inhibit handle stop 1044 from rotating within housing 1002, while spindle end cap 1042 rotates with spindle tube 1024.

Handle stop 1044 further includes a notch for releasably engaging manifold 1008 when adjacent to each other in a fully retracted or closed configuration to lock spindle tube 1024 in axial translation with respect to manifold 1008 and housing 1002 if desired.

A desired length of axial travel of ablation assembly 106 with respect to the working end or tip of the bronchoscope is configured or determined by a total length of shaft 102 of catheter assembly 101, and the relationship of catheter tube 1004 with respect to spindle tube 1024 of the handle assembly 104. In one embodiment, the desired length of travel of ablation assembly 106 with respect to the working end or tip of the bronchoscope is equal to or greater than a longitudinal length of ablation assembly 106. In an embodiment, a longitudinal length of ablation assembly 106 includes a length of an expandable member (e.g. balloon) in addition to the conduit/electrode as seen in FIG. 7; in an alternative embodiment, the longitudinal length of ablation assembly 106 includes the length of the expandable member only. For sake of simplicity, a longitudinal length of ablation assembly 106 is referred to generally, and can incorporate either length.

To demonstrate the relationship, in a non-limiting embodiment, a working length of a commercially available bronchoscope, measured from the proximal opening of the working channel (to which the handle assembly is couplable) to the distal working end or tip (see FIG. 16) is from about 40 to about 80 cm, more particularly from about 50 to about 65 cm, and more particularly from about 55 to about 60 cm. A portion of shaft 102 extending within housing 1002 of handle assembly 101 can be about 15 to about 20 cm in length. A total length of shaft 102 of catheter assembly 101, including the portion within housing 1002 and the length extending through the bronchoscope (but not including the length of ablation assembly 106), is about 55 to about 100 cm, more particularly about 65 to about 85 cm, and more particularly about 70 to about 80 cm. This ensures that shaft 102 can extend through and out of handle housing 1002, and though and out of the bronchoscope when handle assembly 104 is coupled to the bronchoscope. In a particular embodiment, shaft 102 includes additional length such that a distal portion of shaft 102 having ablation assembly 106 coupled thereto is extendable beyond the working end or tip of the bronchoscope such that about 0.1 cm to about 4 cm of shaft 102 is exposed distally of the bronchoscope.

Further, in this embodiment, an ablation assembly 106 comprises a balloon or basket having a longitudinal length from about 1 to about 8 cm, more particularly from about 3 to about 5 cm, and more particularly from about 4 cm. With spindle tube 1024 fixed to scope coupler 1014, handle housing 1002 can travel axially a distance selected so that catheter tube 1004, and therefore a portion of shaft 102, telescopes within or axially translates with respect to spindle tube 1024 of the handle assembly 104 a length of equal to or greater than a longitudinal length of ablation assembly 106. This allows ablation assembly 106 to shift between being fully extended out of the working end or tip (with or without a gap outside of the working end depending on the total length of shaft 102) of the bronchoscope to fully retracted within the working end of the bronchoscope (with or without a gap inside of the working end depending on the total length of shaft 102).

For example, a total length of shaft 102 may be selected such that, when handle assembly 104 is coupled to the bronchoscope and is fully closed or collapsed (e.g. catheter tube 1004 is at maximum nesting position within spindle 1024, herein referred to as "fully closed handle configuration"), a proximal shoulder of the balloon of ablation assembly 106 extends from about 0.1 to about 4.0 cm, and more particularly about 2 cm, beyond the working end of the bronchoscope. When handle assembly 104 is in a "fully extended handle configuration" in which housing 1002 is at a maximum axial distance from scope coupling assembly 103, ablation assembly 106 entirely retracts within the working end to allow for unobstructed visualization of the airway. In this embodiment, the length of travel is greater than the length of the balloon, such as, for example, the length of travel is from about 1 cm+0.1-4.0 cm to about 8.0 cm+0.1-4.0 cm. Optical coupling between the viewing device of the bronchoscope and the balloon occurs at a partial axial extension of handle assembly 106 (i.e. "partially extended handle configuration") in which the proximal shoulder of the balloon abuts the working end of the bronchoscope.

In an alternative embodiment, when handle assembly 104 is in the fully closed handle configuration, a proximal shoulder of the balloon of ablation assembly 106 abuts the working end of the bronchoscope, and is optically coupled to a viewing device positioned on the working end of the bronchoscope. Catheter tube 1004, and therefore a shaft 102, axially translates with respect to spindle tube 1024 at least a distance equal to length of the balloon such that upon full axial extension of handle assembly 104 to the fully extended handle configuration, the entire balloon is retracted into the working end of the bronchoscope.

In another alternative embodiment, when handle assembly 104 is in the fully extended handle configuration, the proximal shoulder of the balloon of ablation assembly 106 abuts the working end of the bronchoscope, and is optically coupled to a viewing device positioned on the working end of the bronchoscope. In this embodiment, ablation assembly 106 is not retractable within the bronchoscope.

In a particularly aspect, the length of travel of handle housing 1002, and hence ablation assembly 106, is from about 1 to about 20% of the total length of shaft 102, and more particularly from about 1 to about 10% of total length of shaft 102. In preferred embodiments, the length of travel of handle housing 1002 relative to spindle tube 1024, and hence ablation assembly 106, is at least the length of ablation assembly 106, preferably being at least about 105% of the length of ablation assembly 106, and more preferably at least about 110% of the length of ablation assembly 106.

In a particularly aspect, spindle tube 1026, catheter tube 1004, or other components of handle assembly 104 can comprise indicator notches or tabs markings, sensors, lighted indicators, or other suitable devices at predetermined position(s) to provide a visual and/or tactile response when the balloon of ablation assembly 106 is physically abutting the working end of the bronchoscope to indicate optical coupling of the viewing device and the ablation assembly, when the ablation assembly has been fully retracted into the bronchoscope, and/or at any of a variety of other desired locations.

Handle housing 1002, and therefore manifold 1008, catheter tube 1004, and catheter shaft 102, are also rotatable with respect to spindle tube 1024 by rotation of handle housing 1002 with respect to the bronchoscope and scope coupler 1014 for fine circumferential adjustment of the ablation assembly within a treatment area. One or more bearings 1038a, b are frictionally affixed to an interior surface of handle housing 1004 to aid smooth rotation of handle housing 1002 about spindle tube 1024. Optionally, because handle stop 1044 rotates with housing 1002 about spindle tube 1024 and spindle end cap 1042, handle stop 1044 and/or spindle tube 1024 can include indentations that provide a tactile indication or "clicks" corresponding to an amount of rotation. For example, a click can correspond to 1 or more degrees of rotation from a neutral position.

As described in the Background section, a fiber optic camera portion of the bronchoscope is fixed in relation to the bronchoscope, such that as the bronchoscope and catheter assembly rotates, the image portrayed remains right side up. This can cause disorientation as to the actual orientation of the ablation assembly within a treatment site, such as an airway. Referring now to FIGS. 16 and 17A-C, in an embodiment, a distal end 2000 of shaft 102 can comprise one or more markers 2002 for indicating an orientation of ablation assembly 106 within a treatment site. In an embodiment, marker 2002 comprises a longitudinal stripe or band, such as a black pad printed band, that longitudinally extends along at least a portion of an exterior of distal end 2000. When the scope coupling assembly 103 and handle assembly 104 are coupled to the bronchoscope, elongate shaft 102 of the catheter assembly 101 is fed through the working channel 201 and through the scope 200, and extends out of the working channel 201 at a working end 200a of scope 200 as depicted in FIG. 16. Because the handle assembly can only be coupled to working channel 201 in one, unique orientation, elongate shaft 102 extends through and out of working channel 201 in a known or initial orientation. In this embodiment, elongate shaft 102 is coupled to the handle assembly such that marker 2002 extends through the bronchoscope such that it is aligned with the center of camera 2004.

Optionally, radioopaque markers (not shown) can be printed or otherwise deposited on the ablation assembly, such as near or on an electrode, such that the orientation of the ablation assembly can be viewed by radiography, fluoroscopy, ultrasound, or other quick confirmation scan.

Band 2002 can also aid in the axial orientation of the ablation assembly with respect to the working end of the bronchoscope. For example, once the ablation assembly is expanded in the airway, it can be retracted closer to the bronchoscope until the band is no longer visible by the camera. This indicates an optimal distance between the balloon or expandable member and the camera such that optical coupling of the ablation assembly is accomplished. This allows the electrode of the ablation assembly to be viewed from the working end of the bronchoscope. The camera can then be moved independently of the ablation assembly.

Braiding 2006 can be incorporated along at least a portion of distal end 2000 of shaft 102. Braiding 2006 gives torsional stability to distal end 2000 so that steering of housing 1002 and manifold 1008 of handle assembly 104 is translated the entire length of shaft 102 so that ablation assembly 106 rotates and axially translates directly in response to handle and/or bronchoscope movements. Braiding 2006 also prevents or inhibits kinking of shaft 102. A small gap of unbraided section 2008 can be included on the end of distal end 2000 so as not to interfere with optical coupling, as described above.

Referring back to FIGS. 5A-5C, once engaged with device 200, a user can maneuver catheter assembly 101 with ablation assembly 106 in the cavity or conduit, such as the airway, in which treatment is taking place. Coarse adjustment of ablation assembly 106 is accomplished via axial and rotational movement of the device 200 such that handle assembly 104, and therefore manifold 1008 and catheter tube 1006, moves with scope coupling assembly 103 and device 200 causing ablation assembly 106 to translate axially and/or rotate.

Fine adjustment of ablation assembly 106 is accomplished via axial and rotational movement (220 and 230) of handle housing 1002 with respect to device 200 and scope coupling assembly 103 as depicted in FIGS. 5A-5C. For example, moving housing 1002 to a refracted axial position relative to delivery device 200 (FIG. 5B), such that catheter tube 1004 is nested within spindle tube 1024, provides maximum extension of the distal end of shaft 102 with ablation assembly 106 relative to the distal portion of device 200 and into the cavity, conduit, or vessel in which the treatment is taking place. This can allow, for example, the user to target a greater range of tissue for treatment. Extension of handle housing 1002 (FIG. 5A), in which catheter tube 1004 is retracted from spindle tube 1024, causes the distal end of shaft 102 and therefore ablation assembly 106 to retract back toward the distal portion of device 200, and in some instances, within the working end of device 200.

In some embodiments, and referring to FIG. 5C, handle housing 1002 functions as a control or steering mechanism for adjusting the circumferential or rotational position of shaft 102 and/or ablation assembly 106. For example, handle housing 1002, and therefore manifold 1008 and catheter tube 1006, can be configured to rotate in predetermined degree increments or continuously with respect to the scope coupler 1014 and device 200. Any of a variety of rotational graduations can be visually and/or tactically (e.g. clicking) incorporated on handle 104, e.g. 1, 5, 10, 20, 30, 45, 90, 120, or 180 degree increments.

Figure 18:
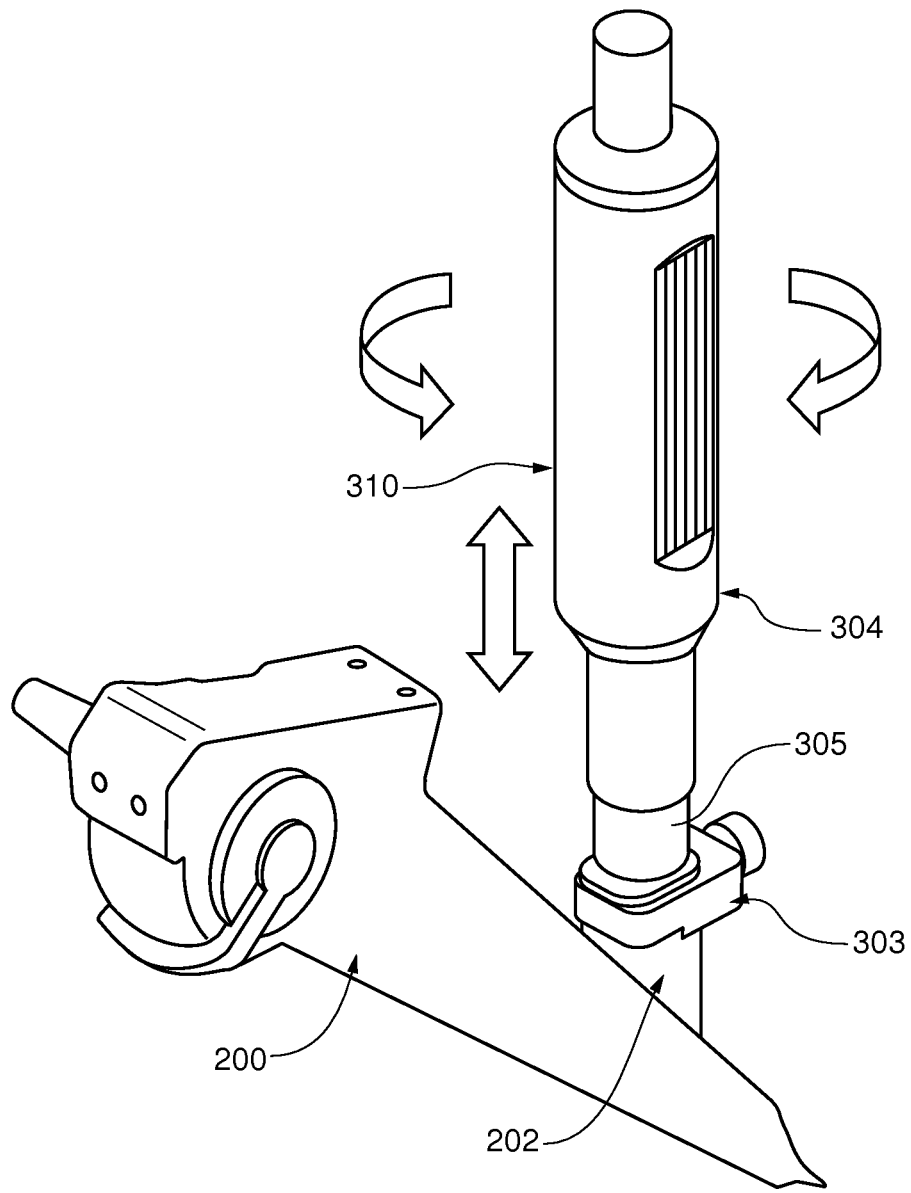
FIG. 18 is an illustration of the axial and circumferential controls of a handle assembly according to an alternative embodiment.

In an alternative embodiment, depicted in FIG. 18, handle assembly 304 includes a control mechanism for circumferential/rotational maneuverability including a body portion 310 configured to rotate about a spindle tube 305 fixed to scope coupler 303, such that when the body portion 310 is rotated circumferentially in one direction, the catheter shaft and ablation assembly rotate circumferentially in the same direction, while device 200, working channel port 202, and scope coupler 303 are fixed. In other embodiments, body portion 310 is also configured to move axially with respect to spindle tube 305 and scope coupler 303, such that when body portion 310 is moved axially in one direction, the catheter shaft and ablation assembly move axially in the same direction with respect to device 200 and scope coupler 303.

Figure 19:
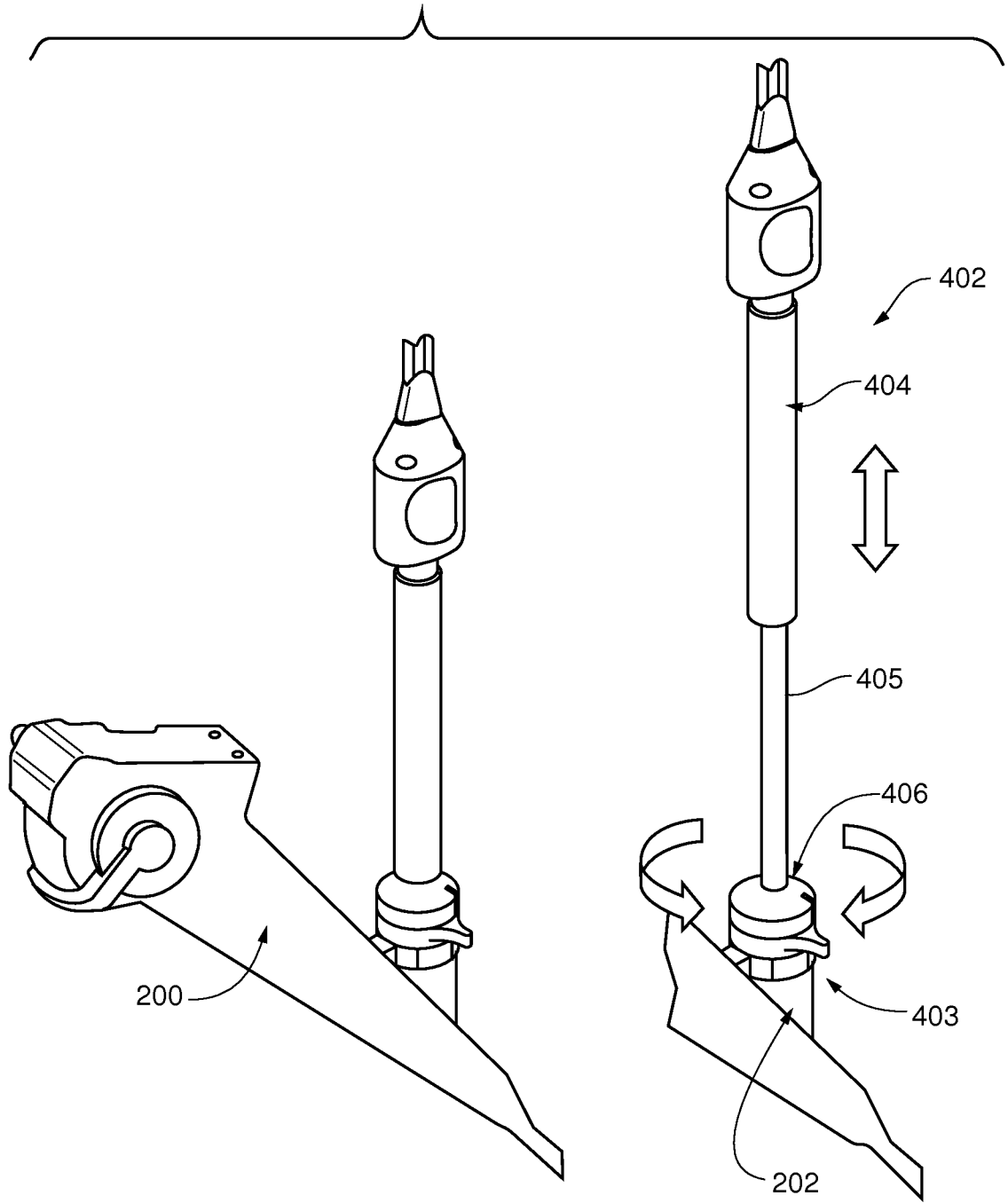
FIG. 19 is an illustration of the handle assembly wherein the axial and circumferential controls are decoupled according to an alternative embodiment.

In alternative embodiments, as depicted in FIG. 19, handle assembly 402 includes a first body portion 404 for axial maneuverability and a second body portion 406 for rotational maneuverability. Handle assembly 402 is coupled to working channel port 202 of scope 200 via scope adapter 403. Adapter 403 is both axially and rotationally fixed with respect to port 202. A spindle tube 405 is axially fixed to adapter 403. Handle assembly 402 can comprise a first body portion 404 configured to translate axially along spindle tube, which translates to axial maneuverability of an ablation assembly fixed to a distal end of the catheter shaft. Second body portion 406, spindle tube 405, and first body portion 404 are configured to rotate about scope adapter 403, which translates to rotationally maneuverability of the ablation assembly.

In still other embodiments (not shown), the controls for axial and circumferential maneuverability can comprise one or more motors, hydraulic or pneumatic cylinders, or other powered manipulators with associated buttons, switches, sensors, etc. configured to maneuver the distal portion of the endoscopic device without the need to manually manipulate a mechanism on the handle. In still other embodiments (not shown), the control mechanisms for precise or fine axial and/or rotational adjustment are automated, such as by servomotors.

Catheter positioning handle assemblies and systems allow for fine adjustment and maneuverability of the catheter shaft and ablation assembly independent of the bronchoscope or other delivery device and accessories coupled to the delivery device, such as cameras and/or lighting sources. For example, the handle can be used to more accurately position the ablation assembly under visualization with a camera or other optical element associated with the bronchoscope through which the catheter is positioned. Preferably the handle will facilitate maneuvering the catheter such that the ablation assembly is visible with the optical element during treatment. In preferred embodiments, the handle will facilitate optically coupling of an expandable member of the catheter assembly with an optical element of the bronchoscope, and a secondary source for visual cues for positioning can be in the form of radiopaque marks or radiopaque indicators on the ablation assembly to indicate fixing the catheter in position of the energy emitter relative to the bronchoscope to maintain such optical coupling during treatment.

According to a non-limiting embodiment, in use, during treatment for a pulmonary disease (e.g., a targeted lung denervation procedure) a bronchoscope can be positioned in the airway according to a typical bronchoscopic procedure. The user can chose the right or left main bronchi. A catheter assembly including a balloon with one or more electrodes coupled thereto can be folded, deflated, or wrapped on the distal end of the shaft of the catheter. The shaft and ablation assembly are inserted into a working channel of the bronchoscope and the handle assembly and scope adapter are connected such that the handle assembly is secured to the bronchoscope. The catheter shaft will then be aligned via the band on the distal end of the catheter shaft such that the user will have knowledge of electrode positioning and orientation relative to the airway by this initial positioning. In some embodiments, markings on shaft can be visible from the bronchoscope, which can aid the user during positioning of electrode. Optionally, radiopaque markers can be incorporated for additional confirmation of position.

The user can position the catheter shaft and ablation assembly within the airway (e.g., right or left bronchi). Coarse adjustments are made by axial and rotational translation of the bronchoscope itself, as the handle moves with the scope. Fine adjustments are made in the airway for treatment (e.g., lung denervating using radiofrequency therapy) using the axial and circumferential controls of the handle that adjust the shaft and ablation assembly relative to the scope (i.e. without moving the scope) to position electrode in a position advantageous for treatment. Once positioned, such as between cartilaginous rings of the airway, the user can inflate the balloon, which in turn causes the electrode(s) to contact the airway wall.

The positioning of the electrode and the balloon in the airway can be informed using a camera coupled to the bronchoscope, such as a lens with fiber optics and/or charge-coupled device (CCD) chip, which provides visual cues as to the position of electrode and balloon, relative to the anatomy of the airway and the other devices. Visualization of the electrode and balloon can be performed by moving the camera independently of the electrode and balloon. For example, the user can hold the handle of catheter assembly fixed, and then axially move the camera towards the electrode and the balloon without disturbing their position. With the ability to hold the handle in a stationary position, the electrode and balloon of the catheter assembly maintain a fixed position in the airway, thus allowing a user to freely move the camera axially and circumferentially for various visual views. Once the desired position is achieved, the user can perform treatment by powering the one or more electrodes, while simultaneously cycling coolant through the cooling circuit, as described above.

In some embodiments, such that when a circumferential lesion is desired, and the electrode size is less than the circumference of the airway, the treatment is repeated. For example, after the initial application of energy, the user deflates the balloon at least partially or fully, such as by stopping or slowing the coolant flow to depressurize balloon and the optional conduit having the electrode thereon. The user can then reposition electrode to a different quadrant rotationally and/or axially displaced from the first quadrant of the tissue by rotating and/or moving the bronchoscope (coarse adjustment) and then the control mechanism on the handle (fine adjustment), which in turn moves the electrode. In some embodiments, the electrode can be adjusted more finely in one or both axial and circumferential directions before ablation using the handle without moving the position of the bronchoscope.

In one particular embodiment, in which the electrode is a quarter of the circumference of the main bronchus, the initial position of the electrode when inserted through the bronchoscope is ventral. When positioned in the left main bronchus, for example, the handle assembly and bronchoscope are then rotated 90 degrees counterclockwise so that the electrode is now positioned in the left lateral quadrant. Fine axial and/or rotational adjustments can be made to the electrode as necessary, and as described above. Confirmation from the camera that the black band is still centered with the camera is made, as well as other optional confirmations. The ablation assembly is pressurized as described above, and energy is supplied to the electrode to ablate the target tissue. Upon completion of treatment, the balloon is at least partly depressurized, and the bronchoscope and handle assembly are together rotated 90 degrees clockwise such that the electrode is now positioned in the ventral quadrant. The treatment is repeated as described. The bronchoscope and handle assembly are then rotated 90 degrees clockwise to the right lateral, and treatment is repeated. Finally, the bronchoscope and handle assembly are rotated 90 degrees clockwise to the dorsal quadrant and treatment is repeated. The catheter assembly can then be retracted into the bronchoscope, and the bronchoscope can be positioned within the right main bronchus, and the therapy repeated, as needed. This clockwise rotation of treatment allows a practitioner to easily, and single handedly rotate the bronchoscope and ablation assembly about the circumference of the airway.

In some embodiments, treatment conditions can require the use of vacuum operation of the bronchoscope, such as to clean an area or the bronchoscope tip. In such embodiments, the entire distal portion of the catheter shaft and ablation assembly can be withdrawn into the working channel of the bronchoscope by pulling the handle so that it is in its fully extended position (See, e.g., FIG. 5A). A vacuum device or aspiration lumen can then be extended through the working channel of the bronchoscope into a position to vacuum debris without compromising the position of the bronchoscope.

Upon completion of treatment, the user can withdraw the entire shaft and ablation assembly of the catheter into the working channel of the bronchoscope by pulling handle 100 to its fully extended position (See, e.g., FIG. 5A), without detachment of the handle from the bronchoscope. This allows the catheter to be out of the view of the bronchoscope camera field of view to facilitate, for example, an assessment of the effectiveness of the treatment. The user can then orient the bronchoscope to the other bronchi for treatment, and the catheter shaft and ablation assembly can be advanced from the bronchoscope working channel into the other bronchi.

Referring now to FIGS. 20A-20F, an embodiment of a bronchoscope adapter assembly is depicted. Adapter assembly 1700 is configured to facilitate coupling of the handle assembly of the catheter assembly as previously described to a working channel port 202 of device 200, the working channel being differently sized or smaller than a port for accommodating coupler assembly 103. Adapter assembly 1700 generally includes a shroud 1702 and a coupler 1720. Shroud (or shell) 1702 comprises a housing portion 1704, a through bore 1706, and an optional alignment tab 1708. Coupler 1720 comprises a flange 1722, a neck portion 1724, a collar portion 1726, a through bore 1727, an alignment slot 1728, one or more optional partial relief slots 1729, and a ledge 1730 on an inner surface of coupler 1720. Flange 1722 may include a tapered face, as depicted in FIGS. 20A-20F, so as to allow handle 104 to be more easily connected to adapter assembly 1700.

Figure 20A:
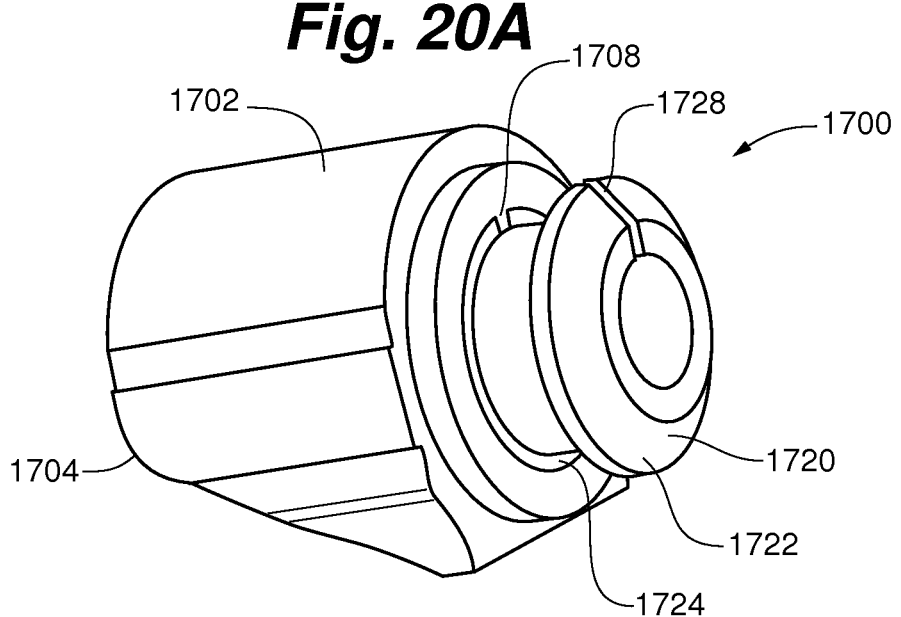
FIG. 20A is a perspective view of a scope adapter assembly including a shroud and a coupler according to an embodiment.
Figure 20B:
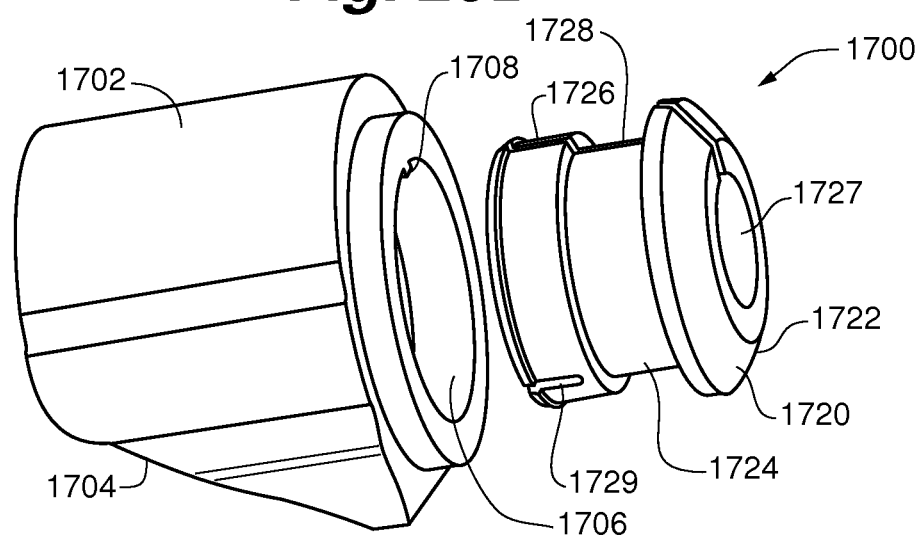
FIG. 20B is an exploded view of the adapter assembly of FIG. 20A.
Figure 20C:
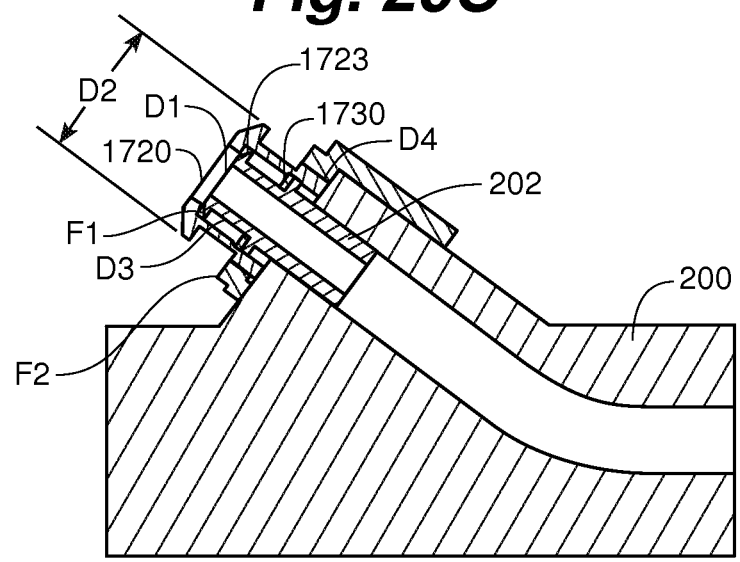
FIG. 20C is a cutaway view of the adapter assembly of FIG. 20A, installed on a delivery device.
Figure 20D:
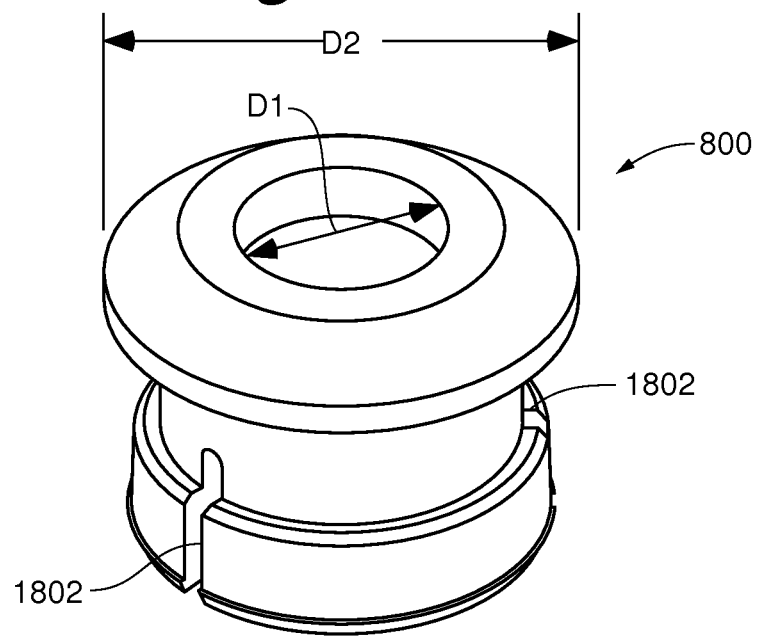
FIG. 20D is a perspective view of an alternative coupler, according to another embodiment.

As shown in FIG. 20D, flange 1722 has an inner diameter D1, and an outer diameter D2. As shown in FIG. 20C, neck portion 1724 has an inner diameter D3 larger than inner diameter D1 of flange 1722 such that at the junction between neck portion 1724 and flange 1722, an abutment ledge 1723 is formed. Abutment ledge 1723 can cooperate with a retaining flange F1 in abutting relationship on an end of port 202.

Collar portion 1726 has a variable inner diameter D4 larger than inner diameter D3 of such that at the junction between neck portion 1724 and collar portion 1726, an abutment ledge 1730 is formed. Abutment ledge 1730 can cooperate with a retaining flange F2 in abutting relationship on an end of port 202, as shown in FIG. 20C.

As shown in FIG. 20B, collar 1726 may include one or more through and/or partial (1728, 1729) relief slots to facilitate expansion and/or contraction which may occur during engagement and/or disengagement of adapter assembly 1700 with port 202.

Figure 20E:
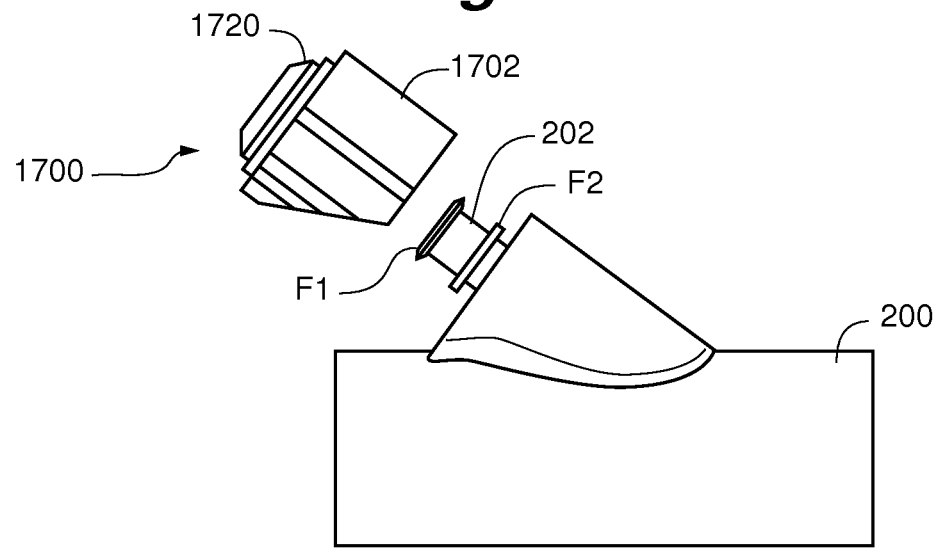
FIG. 20E is a perspective view of an adapter assembly and delivery device in a first position, according to an embodiment.
Figure 20F:
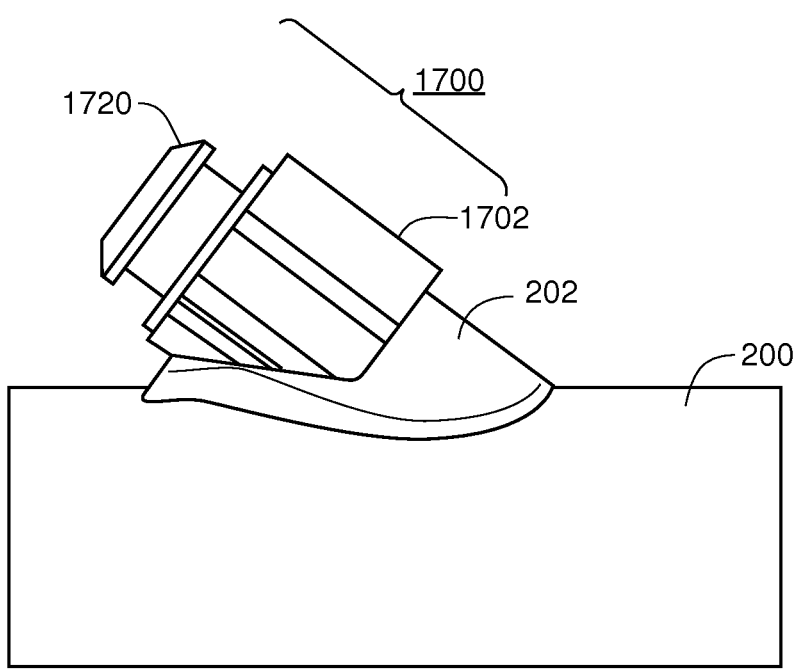
FIG. 20F is a perspective view of the adapter assembly of FIG. 20E attached to the delivery device.

As depicted in FIGS. 20C and 20F, coupler 1720 is installed around the outer perimeter or diameter of port 202, effectively creating a larger interface for coupling assembly 103 of handle 104. Slot 1728 of coupler 1720 is configured to communicate with tab 1708 of shroud 1702. To install adapter assembly 1700 on a port 202 of a device 200, shroud 1702 is first positioned such that bore 1706 is arranged proximate neck portion 1724 of coupler 1720 and such that collar portion 1726 is not constrained, e.g. D4 is at a resting diameter, as depicted in FIG. 20E. Adapter assembly 1700 may then be advanced onto port 202, with collar portion 1726 free to expand (and therefore D4 free to expand) to allow ledge 1730 to be passed over first retaining flange F1 on port 202 and into abutment with second retaining flange F2. Shroud 1702 may then be moved to a locked position wherein bore 1706 of shroud 1702 is aligned with collar portion 1726 of coupler 1720, as depicted in FIG. 20F, thereby squeezing collar portion 1726 to minimize D4 so that it fits securely around port 202. Adapter assembly 1700 is then engaged with port 202 and a handle assembly 104 of a catheter assembly 101 may be connected via adapter assembly 103 to flange 1722 of coupler 1720.

Optionally, slot 1728 may comprise a tapered profile, being wider toward collar portion 1726 and narrower toward flange portion 1722. Such a tapered arrangement of slot 1728 facilitates easier engagement and/or disengagement of adapter assembly 1700 with port 202, in that as shroud 1702 is advanced from collar portion 1726 toward flange 1722 of coupler 1720 to disengage adapter assembly 1700 from port 202, tab 1708 of shroud 1702 advances in the narrowing slot 1728 causing the collar portion 1726 to spread open such that ridge 1730 clears the retaining flange on port 202, allowing adapter assembly 1700 to be removed from port 202.

The dimensions of adapter assembly 1700 may be selected as desired in order to couple with a variety of delivery devices 200.

In an alternative embodiment, the shroud does not include an alignment tab (not shown), allowing an alternative coupler 1800, depicted in FIG. 20D, configured with no through slots and instead with multiple partial relief slots 1802 that facilitate expansion and/or contraction which may occur during engagement and/or disengagement of adapter assembly 1700 with port 202.

Figure 21:
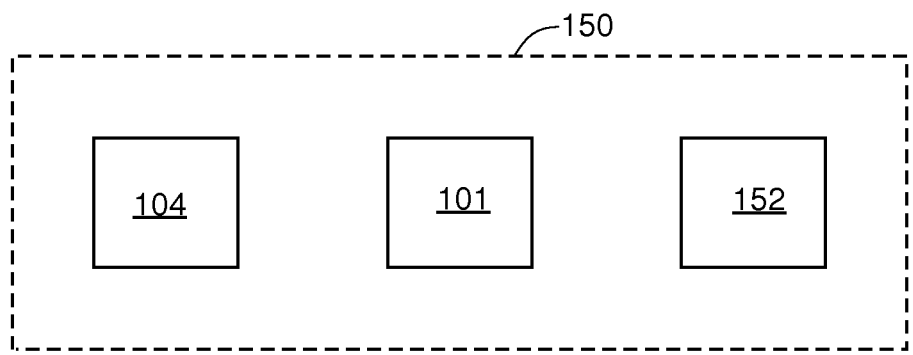
FIG. 21 is a schematic representation of a kit according to an embodiment.

In embodiments, a kit 150 can include a catheter assembly 101 and handle assembly 104 as described above, and a set of instructions 152 for using the contents of 150, such as depicted in FIG. 21. Kit 150 may also include coupling assembly 103 and/or adapter assembly 1700, or adapter assembly 103 and/or adapter assembly 1700 may be provided independently of kit 150. Kit 150 may be comprised of one or more hermetically sealed and sterilized packages. The contents of kit 150 may be provided already assembled as necessary, or the contents may be provided individually and instructions 152 include the steps of coupling together the contents as described herein. The kit 150 and/or the individual contents of kit 150 may be provided by causing the kit and/or contents to be manufactured and made available to a user.

Instructions 152 can be any of a variety of tangible or intangible media including, but not limited to a written manual, a CD or CD-ROM, CD, CD-ROM, DVD, BluRay, digitally downloadable or viewable on onto a personal device, such as a computer, tablet, smart device, and/or via verbal instruction by a provider of the kit 150. In another embodiment, instructions 152 for using the assemblies in accordance with the various embodiments described herein are provided, for example, by a manufacturer or supplier of the assemblies, separately from providing the assemblies, such as by way of information that is accessible using the Internet or by way of seminars, lectures, training sessions or the like.

Embodiments of the present invention thus allow a user to maneuver the catheter shaft and ablation assembly independently from the bronchoscope, and easily and conveniently into a position that facilitates efficient and effective treatment, ultimately improving patient outcomes and decreasing recovery times. Further, the handle assembly coupled to the bronchoscope becomes a pointer or indicator of the ablation assembly within the treatment site to supplement visual cues provided by the bronchoscope viewing device or camera. Finally, the handle assembly coupled to the bronchoscope allows for easy and efficient visual or optical coupling of the bronchoscope viewing device to the ablation assembly.

The handle and catheter systems according to embodiments can be used to maneuver ablation assemblies comprising expandable members and one or more energy emitters or electrodes as described above, and/or can be designed or configured for axially, rotational, and/or other manipulation of any of a variety of treatment assemblies including needle and/or needleless injection or drug delivery systems such as, for example, for the injection or delivery of neurotoxins, sclerosing agents, any of a variety of agents for the treatment of pulmonary disorders. For example, the handle and catheter system can be configured to axially (advancing and retracting) and/or rotationally manipulate one or more needles or ports within and around the airway. Various non-limiting examples of assemblies are described in one or more of the patents and applications listed below, all of which are incorporated by reference in their entireties either herein or above:

U.S. Pat. No. 8,088,127 entitled "Systems, Assemblies, and Method for Treating a Bronchial Tree;"

U.S. Patent Application Publication No. 2011/0152955 entitled "Delivery Devices with Coolable Energy Emitting Assemblies;"

U.S. Patent Application Publication No. 2012/0310233 entitled "Systems, Apparatus, and Methods for Treating Tissue and Controlling Stenosis;"

U.S. Patent Application Publication No. 2011/0118725 entitled Non-invasive and Minimally Invasive Denervation Methods and Systems for Performing the Same;"

U.S. Patent Application Publication No. 2012/0302909 entitled "Methods and Systems for Screening Subjects;"

U.S. Patent Application Publication No. 2011/0301587 entitled "System and Method for Pulmonary Treatment;"

U.S. Pat. No. 8,172,827 entitled "Apparatus for Treating Asthma Using a Neurotoxin;"

U.S. Patent Application Publication No. entitled "Method and Apparatus for Controlling Narrowing of at Least One Airway;"

U.S. Pat. No. 8,483,831 entitled "System and Method for Bronchial Dilation;"

PCT Application Publication No. WO 2013/052501 entitled "Apparatuses and Methods for Injuring Nerve Tissue;"

U.S. Patent Application Publication No. 2013/0310822 entitled "Compact Delivery Pulmonary Treatment System and Method for Improving Pulmonary Function;"

U.S. Provisional Patent Application No. 61/746,460 entitled "Methods for Improving Drug Efficacy;"

U.S. Provisional Patent Application No. 61/779,371 entitled "Fluid Delivery System and Method for Treatment;"

U.S. Provisional Patent Application No. 61/876,925 entitled "Systems, Devices, and Methods for Treating a Pulmonary Disease with Ultrasound Energy;"

U.S. Provisional Patent Application No. 61/847,477 entitled "Methods for Protecting the Esophagus During Pulmonary Treatment Procedures;" and U.S. Provisional Patent Application Nos. 61/799,742 and 61/870,373, both entitled "Systems, Devices, and Methods for Treating a Pulmonary Disorder with an Agent."

It should also be appreciated that the exemplary embodiment or exemplary embodiments are only examples, and are not intended to limit the scope, applicability, or configuration of the subject matter hereof in any way. Rather, the foregoing detailed description will provide those skilled in the art with an enabling disclosure for implementing the exemplary embodiment or exemplary embodiments. It should be understood that various changes can be made in the function and arrangement of elements without departing from the scope of the subject matter hereof as set forth in the appended claims and the legal equivalents thereof.

The embodiments above are intended to be illustrative and not limiting. Additional embodiments are within the claims. Although the present subject matter has been described with reference to particular embodiments, workers skilled in the art will recognize that changes may be made in form and detail without departing from the spirit and scope of the subject matter hereof.

Various modifications to the subject matter hereof may be apparent to one of skill in the art upon reading this disclosure. For example, persons of ordinary skill in the relevant art will recognize that the various features described for the different embodiments of the subject matter can be suitably combined, un-combined, and re-combined with other features, alone, or in different combinations, within the spirit of the subject matter hereof. Likewise, the various features described above should all be regarded as example embodiments, rather than limitations to the scope or spirit of the subject matter hereof. Therefore, the above is not contemplated to limit the scope of the present subject matter hereof.

For purposes of interpreting the claims for the present subject matter, it is expressly intended that the provisions of Section 112, sixth paragraph of 35 U.S.C. are not to be invoked unless the specific terms "means for" or "step for" are recited in a claim.

What is claimed is:

1. A catheter and handle assembly configured to be coupled to a delivery device, the delivery device having a proximal working port, a distal working end, and a working channel extending between the proximal working port and the distal working end thereby defining a working length, the assembly comprising:
   a catheter assembly including
      an elongate shaft, and
      an ablation assembly coupled to a first end of the elongate shaft, the ablation assembly comprises an expandable member having an energy emitter thereon, the expandable member being movable between a first retracted state and a second expanded state, and a coolant fluid path for circulating coolant therethrough to cool the energy emitter and/or a surface of the expandable member; and
   a handle assembly coupled to a second end of the elongate shaft, the handle assembly including
      a handle frame and a control, the control being movable relative to and over the handle frame and coupled to the elongate shaft, wherein the control comprises a body positioned over the handle frame and a bearing frictionally affixed to an interior surface of the body, wherein the second end of the elongate shaft is coupled to the body, and wherein the body is configured to rotate about the handle frame via the bearing when the catheter and handle assembly is coupled to the delivery device to rotate the ablation assembly with respect to the delivery device when the expandable member is in the second expanded state, and wherein the body is configured to move axially along the handle frame to move the ablation assembly axially with respect to the delivery device between a first position and a second position, wherein the handle frame is configured to telescope into and out of the control, and
      wherein a first portion of the elongate shaft is configured to extend within and through the working channel of the delivery device when the catheter and handle assembly is operably coupled to the delivery device.

2. The catheter and handle assembly of claim 1, wherein moving the control moves both the elongate shaft and the ablation assembly relative to the delivery device.

3. The catheter and handle assembly of claim 1, wherein the catheter and handle assembly further comprises a coupling assembly configured to couple to the handle assembly and the working port of the delivery device, the coupling assembly configured to remain fixed relative to the delivery device and the handle frame while the control is moved to move the ablation assembly, wherein the coupling assembly comprises a coupler and a locking mechanism for securing the handle assembly to the proximal working port of the delivery device.

4. The catheter and handle assembly of claim 1, wherein, when the body is rotated in one direction, the ablation assembly rotates in the same direction.

5. The catheter and handle assembly of claim 1, wherein the body comprises a handle housing rotationally coupled to the handle frame.

6. The catheter and handle assembly of claim 1, wherein, when the body is moved axially in one direction, the shaft and ablation assembly move axially in a same direction as the one direction.

7. The catheter and handle assembly of claim 1, wherein the control is shiftable between a first state and a second state relative to the handle frame, the control being coupled to the elongate shaft such that shifting the control moves the ablation assembly in the axial direction relative to the handle frame,
   wherein in the first state, the ablation assembly is retracted within the working channel, wherein in the second state, the ablation assembly extends beyond the working end of the delivery device, and
   wherein the first portion of the elongate shaft of the catheter assembly has a nominal catheter length equal to or greater than the working length of the delivery device.

8. The catheter and handle assembly of claim 7, wherein the nominal catheter length enables optical coupling of the ablation assembly with a viewing device coupled to or integrated with the working end of the delivery device.

9. The catheter and handle assembly of claim 7, wherein the control is shiftable to an intermediate state between the first and second states such that a portion of the ablation assembly is retracted within the working channel.

10. The catheter and handle assembly of claim 9, wherein an entirety of the ablation assembly is retracted within the working channel when the control is in the first state.

11. The catheter and handle assembly of claim 7, wherein the nominal catheter length is greater than the working length of the delivery device such that the ablation assembly is configured to extend beyond the working end of the delivery device a distance from about 0.1 cm to about 4.0 cm when the control is in the second state.

12. The catheter and handle assembly of claim 7, wherein a total travel length of the ablation assembly when the control shifts between the first state and the second state is equal to or greater than a longitudinal length of the ablation assembly.

13. The catheter and handle assembly of claim 12, wherein the total travel length of the ablation assembly is from about 1% to about 20% of the nominal catheter length.

14. The catheter and handle assembly of claim 13, wherein the total travel length of the ablation assembly is from about 1% to about 10% of the nominal catheter length.

15. The catheter and handle assembly of claim 1, wherein the handle further comprises a connector for connection to a power cord.

16. The catheter and handle assembly of claim 1, wherein the handle assembly further comprises internal batteries as a power source.

17. The catheter and handle assembly of claim 1, wherein the handle assembly further comprises a fluid junction for connection to a fluid source.

18. The catheter and handle assembly of claim 1, wherein the first end of the elongate shaft includes a fluoroscopically visible indicator device, wherein the fluoroscopically visible indicator device indicates alignment of the ablation assembly relative to the delivery device.

19. The catheter and handle assembly of claim 18, wherein the fluoroscopically visible indicator device comprises an elongate stripe along an external surface of the first end of the elongate shaft, the stripe being substantially parallel to the elongate shaft.

20. The catheter and handle assembly of claim 1, wherein the ablation assembly comprises radiopaque markers for indicating a position of the ablation assembly relative to the delivery device under fluoroscopic visualization.

21. The catheter and handle assembly of claim 1, wherein the assembly further comprises the delivery device, wherein the delivery device to which the catheter and handle assembly is configured to be coupled comprises a bronchoscope.

22. The catheter and handle assembly of claim 1, the catheter assembly including a pressure tube extending from a second end of the catheter and along the elongate shaft and into the expandable member of the ablation assembly, wherein a first end of the pressure tube is operably coupled to a pressure sensor positioned on or proximate the handle assembly, and a second end of the pressure tube is positioned in the expandable member and includes at least one aperture, such that the pressure sensor is configured to sense a pressure in the expandable member.

23. The catheter and handle assembly of claim 22, wherein the pressure tube is formed of Nitinol.

24. A catheter and handle kit comprising:
a catheter and handle assembly comprising:
an elongate shaft;
an ablation assembly coupled to a first end of the elongate shaft, the ablation assembly comprises an expandable member having an energy emitter thereon, the expandable member being movable between a first retracted state and a second expanded state, and a coolant fluid path for circulating coolant therethrough to cool the energy emitter and/or a surface of the expandable member;
a handle fixed to a second end of the elongate shaft, the handle including a first portion, and a second portion axially and rotationally movable over the first portion via a bearing frictionally affixed to an interior surface of the second portion to axially and rotationally manipulate the expandable member; and
a coupling assembly coupled to the handle and couplable to a port of a delivery device, wherein the first portion of the handle is fixed relative to the coupling assembly, and the second portion of the handle is movable relative to and over the first portion and the coupling assembly such that the second portion is configured to move the ablation assembly relative to the delivery device in an axial direction when the second portion is moved in the axial direction relative to the first portion, and a rotational direction when the second portion is rotated about the first portion with the coupling assembly remaining fixed relative to the delivery device, and wherein the first portion is configured to nest within the second portion; and
a set of instructions configured for use with the catheter and handle assembly, the set of instructions comprising a recitation of steps including:
positioning the ablation assembly in a lumen of a subject by moving the ablation assembly through the working channel of the delivery device;
coupling the first portion of the handle to the delivery device; and
moving the second portion of the handle while the first portion remains fixed to the delivery device so as to move the ablation assembly axially and circumferentially into a position in the lumen to administer a treatment to the subject.

\* \* \* \* \*